(12) United States Patent
Tavernier et al.

(10) Patent No.: US 10,407,480 B2
(45) Date of Patent: *Sep. 10, 2019

(54) TARGETED MODIFIED TNF FAMILY MEMBERS

(71) Applicants: VIB VZW, Ghent (BE); UNIVERSITEIT GENT, Ghent (BE); CENTRE NATIONAL DE LA RECHERCHE SCIENTIFIQUE, Paris (FR); UNIVERSITÉ DE MONTPELLIER, Montpellier (FR); CENTRE HOSPITALIER REGIONAL UNIVERSITAIRE DE MONTPELLIER, Montpellier (BE)

(72) Inventors: Jan Tavernier, Balegem (BE); Jennyfer Bultinck, Ledeberg (BE); Frank Peelman, Gentbrugge (BE); Gilles Uze, Montpellier (FR)

(73) Assignees: VIB VZW, Ghent (BE); UNIVERSITEIT GENT, Ghent (BE); UNIVERSITÉ DE MONTPELLIER, Montpellier (FR); CENTRE NATIONAL DE LA RECHERCHE SCIENTIFIQUE, Paris (FR); CENTRE HOSPITALIER REGIONAL UNIVERSITAIRE DE MONTPELLIER, Montpellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/020,469

(22) Filed: Jun. 27, 2018

(65) Prior Publication Data

US 2018/0298074 A1 Oct. 18, 2018

Related U.S. Application Data

(60) Continuation of application No. 15/883,925, filed on Jan. 30, 2018, now Pat. No. 10,035,835, which is a division of application No. 14/905,354, filed as application No. PCT/EP2014/065554 on Jul. 18, 2014, now Pat. No. 9,914,759.

(30) Foreign Application Priority Data

Jul. 19, 2013 (EP) ..................................... 13306046

(51) Int. Cl.
| | | |
|---|---|---|
| C07K 14/525 | (2006.01) | |
| C07K 16/32 | (2006.01) | |
| A61K 39/00 | (2006.01) | |
| A61K 38/00 | (2006.01) | |
| C07K 16/28 | (2006.01) | |

(52) U.S. Cl.
CPC ........ C07K 14/525 (2013.01); C07K 16/2869 (2013.01); C07K 16/32 (2013.01); A61K 38/00 (2013.01); A61K 2039/505 (2013.01); C07K 2317/569 (2013.01); C07K 2319/00 (2013.01); C07K 2319/74 (2013.01)

(58) Field of Classification Search
CPC .. C07K 14/525; C07K 16/2869; C07K 16/32; C07K 2319/74; C07K 2319/00; C07K 2317/569; A61K 38/00; A61K 2039/505
See application file for complete search history.

(56) References Cited

U.S. PATENT DOCUMENTS

| 5,914,254 | A | 6/1999 | Mascarenhas et al. |
|---|---|---|---|
| 8,450,460 | B2 | 5/2013 | Hill et al. |
| 8,980,267 | B2 | 3/2015 | Grewal et al. |
| 9,139,634 | B2 | 9/2015 | Morrison et al. |
| 9,534,056 | B2 | 1/2017 | Grewal et al. |
| 9,724,390 | B2 | 8/2017 | Gurney |
| 2010/0172868 | A1 | 7/2010 | Morrison et al. |
| 2010/0297076 | A1 | 11/2010 | Morrison et al. |
| 2011/0104112 | A1 | 5/2011 | Morrison et al. |
| 2011/0274658 | A1 | 11/2011 | Silver et al. |
| 2013/0183298 | A1 | 7/2013 | Le et al. |
| 2015/0139951 | A1 | 5/2015 | Grewal et al. |

FOREIGN PATENT DOCUMENTS

| WO | 9102754 A1 | 3/1991 |
|---|---|---|
| WO | WO 2003092737 A1 | 11/2003 |
| WO | 2006053883 A1 | 5/2006 |

(Continued)

OTHER PUBLICATIONS

Acres, B., et al., "Fusokine Interleukin-2/Interleukin-18, a Novel Potent Innate and Adaptive Immune Stimulator with Decreased Toxicity", Cancer Res., vol. 65, No. 20, (2005), pp. 9536-9546.

Baba, M., et al., "Identification of CCR6, the Specific Receptor for a Novel Lymphocyte-Directed CC Chemokine LARC", The Journal of Biological Chemistry vol. 272, No. 23, (1997), pp. 14893-14898.

Camacho, N.P., et al., "Structure of an Interleukin-1β Mutant With Reduced Bioactivity Shows Multiple Subtle Changes in Conformation That Affect Protein-Protein Recognition", Biochemistry, vol. 32, No. 34, (1993), pp. 8749-8757.

(Continued)

Primary Examiner — Ruixiang Li
(74) Attorney, Agent, or Firm — Morgan, Lewis & Bockius LLP

(57) ABSTRACT

The present invention relates to a modified cytokine of the TNF superfamily, with reduced activity to its receptor, wherein said modified cytokine is specifically delivered to target cells. Preferably, said modified cytokine is a single chain variant of the TNF superfamily, even more preferably, one or more of the chains can-y one or more mutations, resulting in a low affinity to the receptor, wherein said mutant cytokine is specifically delivered to target cells. The targeting is realized by fusion of the modified cytokine of the TNF superfamily to a targeting moiety, preferably an antibody or antibody-like molecule. The invention relates further to the use of such targeted modified cytokine of the TNF superfamily to treat diseases.

6 Claims, 15 Drawing Sheets

Specification includes a Sequence Listing.

(56) References Cited

FOREIGN PATENT DOCUMENTS

| | | |
|---|---|---|
| WO | 2006115800 A2 | 11/2006 |
| WO | 2008014612 A1 | 2/2008 |
| WO | 2008124086 A2 | 10/2008 |
| WO | 2009003145 A1 | 12/2008 |
| WO | 2009039409 A1 | 3/2009 |
| WO | 2010036918 A2 | 4/2010 |
| WO | 2010066740 A1 | 6/2010 |
| WO | 2011020783 A2 | 2/2011 |
| WO | 2011029870 A1 | 3/2011 |
| WO | 2012170072 A1 | 12/2012 |
| WO | 2013059885 A2 | 5/2013 |
| WO | 2013107791 A1 | 7/2013 |
| WO | 2013134138 A1 | 9/2013 |

OTHER PUBLICATIONS

Coulstock, E., et al., "Liver-Targeting of Interferon-Alpha with Tissue Specific Domain Antibodies." PLOS ONE, vol. 8, No. 2, (2013), pp. 1-11.
De Bruyn, M., et al., "Antibody-Based Fusion Proteins to Target Death Receptors in Cancer", Cancer Letters, vol. 332, (2013), pp. 175-183.
Dijkmans, R., et al., "Murine Interferon-Γ/Interleukin-1 Fusion Proteins Used as Antigens for the Generation of Hybridomas Producing Monoclonal Anti-Interleukin-1 Antibodies", Cytokine, vol. 3, No. 2, (1991), pp. 134-140.
Dimitrov, D. S., "Engineered CH2 Domains (Nanoantibodies)", mAbs, Landes Bioscience, vol. 1, No. 1, (2009), pp. 26-28.
Frey, K., et al., "Antibody-Based Targeting of Interferon-Alpha to the Tumor Neovasculature: A Critical Evaluation", Integrative Biology, vol. 3, (2011), p. 468-478.
Garcin, G., et al., "High Efficiency Cell-Specific Targeting of Cytokine Activity", Nature Communications, (2014), pp. 1-9.
Holler, N., et al: "Two Adjacent Trimeric Fas Ligands are Required for Fas Signaling and Formation of a Death-Inducing Signaling Complex", Molecular and Cellular Biology, vol. 23, No. 4, (2003), pp. 1428-1440.
Huang, T., et al., "A Trimeric Anti-HER2/neu ScFv and Tumor Necrosis Factor-[alpha] Fusion Protein Induces HER2/Neu Signaling and Facilitates Repair of Injured Epithelia", The Journal of Pharmacology and Experimental Therapeutics, vol. 316, No. 3, (2006), pp. 983-991.
International Search Report and Written Opinion in PCT/EP2013/050787, dated Jun. 14, 2011.
International Search Report and Written Opinion PCT/EP2014/063976, dated Oct. 29, 2014.
International Search Report and Written Opinion PCT/EP2014/064227, dated Feb. 5, 2015.
International Search Report and Written Opinion PCT/EP2014/064283, dated Oct. 1, 2014.
International Search Report and Written Opinion PCT/EP2014/065554, dated Oct. 30, 2014.
Krippner-Heidenreich, A., et al: "Single-Chain TNF, a TNF Derivative with Enhanced Stability and Antitumoral Activity", The Journal of Immunology, vol. 180, (2008), pp. 8176-8183.
Masci, P. et al., "New and Modified Interferon alfas: Preclinical and Clinical Data", Current Oncology Reports, vol. 5, (2003), pp. 108-113.
Pan, M., et al., "Mutation of the IFNAR-1 Receptor Binding Site of Human IFN-[alpha]2 Generates Type I IFN competitive Antagonists", Biochemistry, vol. 47, (2008), pp. 12018-12027.
Penafuerte, C., et al., "The Human Ortholog of Granulocyte Macrophage Colony-Stimulating Factor and Interleukin-2 Fusion Protein Induces Potent Ex Vivo Natural Killer Cell Activation and Maturation", Cancer Res, vol. 69, No. 23, (2009), pp. 9020-9028.
Rafei, M., et al., "A MCP1 Fusokine with CCR2-Specific Tumoricidal Activity", Molecular Cancer, vol. 10, No. 121, (2011), pp. 1-11.
Rafei, M., et al., "An Engineered GM-CSF-CCL2 Fusokine Is a Potent Inhibitor of CCR2-Driven Inflammation as Demonstrated in a Murine Model of Inflammatory Arthritis", The Journal of Immunology, vol. 183, (2009), pp. 1759-1766.
Roisman, LC., et al., "Structure of the Interferon-Receptor Complex Determined by Distant Constraints from Double Mutant Cycles and Flexible Docking", PNAS, vol. 98, No. 23, (2001), pp. 13231-13236.
Rovero S et al., "Insertion of the DNA for the 163-171 Peptide of IL 1β Enables a DNA Vaccine Encoding p185neu to Inhibit Mammary Carcinogenesis in Her-2/neu Transgenic BALB/c Mice", Gene Therapy, vol. 8, (2001), pp. 447-452.
Schutyser, E., et al., "The CC Chemokine CCL20 and its Receptor CCR6", Cytokine & Growth Factor Reviews, vol. 14, (2003), pp. 409-426.
Weber, H., et al., "Single Amino Acid Changes that Render Human IFN-[alpha]2 Biologically Active on Mouse Cells", The EMBO Journal, vol. 6, No. 3, (1987), pp. 591-598.
Bremer et al., Superior activity of fusion protein scFvRit:sFasL over cotreatment with rituximab and Fas agonists. Cancer Res. 68:597-604, 2008.
Boschert et al., Single chain TNF derivatives with individually mutated receptor binding sites reveal differential stoichiometry of ligand receptor complex formation for TNFR1 and TNFR2. Cellular Signalling 22 (7):1088-1096, 2010.
Loetscher et al., J. Biol. Chem. 268(35):26350-26357, 1993.

A

B

A

B

A

B

A

B

A

B

A

B

A

B

A

B

A

B

A

B

A

B

A

B

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Linker

<400> SEQUENCE: 1

Gly Gly Gly Gly Ser
1               5

<210> SEQ ID NO 2
<211> LENGTH: 49
<212> TYPE: DNA
<213> ORGANISM: Artificial Sequence
<220> FEATURE:
<223> OTHER INFORMATION: Primer

<400> SEQUENCE: 2
gtcaagatct ggcggttcgg cggccgcaat ggcccaggtg cagctgcag           49

<210> SEQ ID NO 3
<211> LENGTH: 67
<212> TYPE: DNA
<213> ORGANISM: Artificial Sequence
<220> FEATURE:
<223> OTHER INFORMATION: Primer
```

```
<400> SEQUENCE: 3
cagttctaga ttacttatcg tcgtcatcct tgtaatccga accgccgtcc ggagaggaga    60
cggtgac                                                              67

<210> SEQ ID NO 4
<211> LENGTH: 51
<212> TYPE: DNA
<213> ORGANISM: Artificial Sequence
<220> FEATURE:
<223> OTHER INFORMATION: Primer

<400> SEQUENCE: 4
gatctggcgg ttcggcggcc gcagattaca aggatgacga cgataagtaa t             51

<210> SEQ ID NO 5
<211> LENGTH: 51
<212> TYPE: DNA
<213> ORGANISM: Artificial Sequence
<220> FEATURE:
<223> OTHER INFORMATION: Primer

<400> SEQUENCE: 5
ctagattact tatcgtcgtc atccttgtaa tctgcggccg ccgaaccgcc a             51

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
tatgatgtgc ccgactacgc tggcggcagc a                                   31

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
gatctgctgc cgccagcgta gtcgggcaca tca                                 33

<210> SEQ ID NO 8
<211> LENGTH: 62
<212> TYPE: DNA
<213> ORGANISM: Artificial Sequence
<220> FEATURE:
<223> OTHER INFORMATION: Primer

<400> SEQUENCE: 8
catatgatgt gcccgactac gctggcggca gcagctctag aaccccccagc gataagcctg    60 tg                                                                   62

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
gtcgaccagg gcaatgatgc cgaagt                                         26
```

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tgacactggc aaaacaatgc a                                      21

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ggtccttttc accagcaagc t                                      21

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gacagccact cacctcttca                                        20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
agtgcctctt tgctgctttc                                        20

<210> SEQ ID NO 14
<211> LENGTH: 157
<212> TYPE: PRT
<213> ORGANISM: Homo sapiens

<400> SEQUENCE: 14

Val Arg Ser Ser Ser Arg Thr Pro Ser Asp Lys Pro Val Ala His Val
1               5                   10                  15

Val Ala Asn Pro Gln Ala Glu Gly Gln Leu Gln Trp Leu Asn Arg Arg
            20                  25                  30

Ala Asn Ala Leu Leu Ala Asn Gly Val Glu Leu Arg Asp Asn Gln Leu
        35                  40                  45

Val Val Pro Ser Glu Gly Leu Tyr Leu Ile Tyr Ser Gln Val Leu Phe
    50                  55                  60

Lys Gly Gln Gly Cys Pro Ser Thr His Val Leu Leu Thr His Thr Ile
65                  70                  75                  80

Ser Arg Ile Ala Val Ser Tyr Gln Thr Lys Val Asn Leu Leu Ser Ala
                85                  90                  95

Ile Lys Ser Pro Cys Gln Arg Glu Thr Pro Glu Gly Ala Glu Ala Lys
            100                 105                 110

Pro Trp Tyr Glu Pro Ile Tyr Leu Gly Gly Val Phe Gln Leu Glu Lys

-continued

```
            115                 120                 125
Gly Asp Arg Leu Ser Ala Glu Ile Asn Arg Pro Asp Tyr Leu Asp Phe
        130                 135                 140

Ala Glu Ser Gly Gln Val Tyr Phe Gly Ile Ile Ala Leu
145                 150                 155
```

TARGETED MODIFIED TNF FAMILY MEMBERS

CROSS-REFERENCE TO RELATED APPLICATIONS

This application is continuation of U.S. application Ser. No. 15/883,925 filed on Jan. 30, 2018, which is a divisional application of U.S. application Ser. No. 14/905,354 filed on Jan. 15, 2016, now U.S. Pat. No. 9,914,759 issued on Mar. 13, 2018, which is the U.S. National Stage Application of International Application No. PCT/EP2014/065554 filed on Jul. 18, 2014, which claims the benefit of and priority to European Application No. 13306046.7 filed on Jul. 19, 2013, the contents of which are incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ORN005D2 ST25.txt; date recorded: Jun. 27, 2018; file size: 4,478 bytes).

The present invention relates to a modified cytokine of the TNF superfamily, with reduced activity to its receptor, wherein said modified cytokine is specifically delivered to target cells. Preferably, said modified cytokine is a single chain variant of a member of the TNF superfamily, even more preferably, one or more of the chains carry one or more mutations, resulting in a low affinity to the receptor, wherein said mutant cytokine is specifically delivered to target cells. The targeting is realized by fusion of the modified cytokine of the TNF superfamily to a targeting moiety, preferably an antibody or antibody-like molecule. The invention relates further to the use of such targeted modified cytokine of the TNF superfamily to treat diseases.

The TNF superfamily consists of pro-inflammatory cytokines with crucial functions in the immune system by regulating cell death, proliferation and differentiation. In addition, members of the family were described to exert functions on bone metabolism, the nervous system, on neo-vasculature and carcinogenesis. It contains 19 ligands, type II (intracellular N terminus and extracellular C terminus) transmembrane proteins, which are biologically active as self-assembling, non-covalent bound homotrimers. Although most TNF superfamily ligands are synthesized as membrane-bound proteins, soluble forms can be generated by proteolytic cleavage. All of them bind to one or more molecules from the TNF receptor superfamily through their C-terminal TNF homology domain, which exhibits—20-30% sequence homology between family members. So far, 29 TNF superfamily receptors have been identified in humans. These are primarily type I (extracellular N terminus, intracellular C terminus) transmembrane glycoproteins with a cystein-rich motif in the ligand-binding extracellular domain. However, there are some exceptions like TRAIL-R3 that is attached to the membrane by a covalently linked C-terminal glycolipid. Soluble receptors can be generated by proteolytic cleavage (e.g. TNF-R1 and TNF-R2) or by alternative splicing of the exon encoding the transmembrane domain. The receptors of this superfamily can be divided in 3 groups based on their signaling properties: receptors with a cytoplasmic death domain that induce apoptosis; receptors with a TRAF-interacting motif that induce several signaling pathways such as NF-κB, JNK, p38, ERK and P13K; and the decoy receptors that lack intracellular signaling domains. TNF induces apoptosis through interaction with TNF-R1 (p55), while binding to TNF-R2 (p75, primarily expressed on immune cells) promotes proliferation. TRAIL signaling is more complex as it can bind to two death receptors (TRAIL-R1 (DR4) and TRAIL-R2 (DR5)), to two decoy receptors (TRAIL-R3 (DCR1) and TRAIL-R4 (DCR2)) and to the soluble osteoprotegerin (OPG). Binding to one of the latter three receptors inhibits TRAIL-mediated apoptosis as it tethers TRAIL away from the death receptors (Gaur and Aggerwal, 2003; Hehlgans and Pfeffer, 2005; Huang and Sheikh, 2007).

The death-inducing TNF superfamily members TNF, CD95L (FasL) and TRAIL are potential therapeutics for cancers that express their respective receptor TNF-R1, CD95, TRAIL-R1 and TRAIL-R2. In fact, TNF was originally discovered more than 25 years ago as a factor with extraordinary antitumor activity, by causing hemorrhagic necrosis of certain tumors in vivo. Later it became clear that the selective damage attributed by TNF to tumor neovasculature also defines its anti-tumor potential (Lejeune et al., 2006; van Horssen et al., 2006). Unfortunately, systemic use of TNF in cancer treatment is still hampered by its shock-inducing properties. It is currently only clinically used in the setting of isolated limb perfusion in combination with chemotherapy to treat soft tissue sarcomas and in-transit melanoma (Roberts et al., 2011). Also CD95L is toxic when administered systemically as it causes lethal hepatotoxicity due to massive hepatocyte apoptosis (Galle et al., 1995). TRAIL, however, has been shown to induce apoptosis in cancer cells with little or no cytotoxicity against non-transformed cells, and clinical trials in various advanced cancers report stable disease in many cases. Still, to obtain sufficient overall therapeutic activity combined treatment is required, which implies possible side effects due to sensitization of normal cells to TRAIL-induced apoptosis (Ashkenazi and Herbst, 2008; Falschlehner et al., 2009). Different approaches have been undertaken to minimize the toxicity upon systemic administration of death-inducing TNF superfamily members, such as mutant TNF with lower toxicity and higher efficiency (Li et al., 2012), delivery of TNF or TRAIL, normally as a single chain construct, by tumor-specific moieties (de Bruyn et al., 2013; Gregorc et al., 2009; Liu et al., 2006; Siegemund et al., 2012; Wang et al., 2006), chimeric soluble CD95L (Daburon et al., 2013) or agonistic TRAILR 1-, TRAIL-R2 or CD95-specific antibodies (Johnstone et al., 2008; Ogasawara et al., 1993; Fox et al., 2010). Some of them can increase the therapeutic index but never to such an extent that it dramatically improves clinical outcome.

Surprisingly, we found that it is possible to make a construct comprising a cytokine of the TNF superfamily, wherein the cytokine is modified to lower the affinity towards the receptor, wherein said cytokine is linked to a targeting moiety, and wherein said construct has a strongly reduced systemic toxicity, and only shows significant biological activity towards the cells that are targeted by the targeting moiety.

A first aspect of the invention is a construct, comprising (i) three copies of a cytokine chain of the TNF superfamily, wherein the resulting cytokine is modified (referred to as "modified cytokine") so that the affinity towards its receptor is lowered, (ii) a linker sequence and (iii) a targeting moiety, wherein said linker sequence is linking the cytokine copies to the targeting moiety. A construct, as used here, can be any proteinaceous construct known to the person skilled in the art, including, but not limited to chemically modified proteins, protein complexes and fusion proteins. In one preferred embodiment, individual, self-trimerizing cytokine chains are used, wherein one or more of the chains may be linked to the targeting moiety. In another preferred embodiment, the three copies are presented as a single chain cytokine; in a preferred embodiment, the copies are separated by a linker sequence to facilitate the presentation of the cytokine in a trimeric form. It is clear for the person skilled in the art that mixed forms, with one free cytokine chain and two cytokine copies linked to each other, are also possible. The resulting trimeric cytokine carries a modification that lowers its biological activity, compared to the wild type cytokine. Such a modification can be a modification that decreases the activity of the normal wild type cytokine, or it can be a modification that increases the activity of a homologous, non-endogenous TNF family cytokine (such as, but not limited to, a TNF family cytokine of another species that is not binding to a human TNF family cytokine receptor). Modifications can be any modification reducing or increasing the activity, known to the person skilled in the art, including but not limited to chemical and/or enzymatic modifications such as pegylation and glycosylation, fusion to other proteins, and mutations. In case two or more copies of the cytokine are presented as a single chain, the length of the linker may be adapted to disturb the normal trimeric structure, resulting in a lower activity toward the receptor. Alternatively, special amino acids may be incorporated in the linker to modify the structure; said amino acids may further be modified. As a non-limiting example, a lysine may be incorporated in the linker to allow pegylation. Preferably said modification is a mutation, even more preferably it is a mutation decreasing the affinity of cytokine towards its receptor. A reduced affinity and a consequent reduced biological activity as used here means that the modified cytokine has a biological activity of less than 70% of the biological activity of the wild type cytokine, even more preferably less than 60% of the biological activity of wild type cytokine, more preferably less than 50% of the biological activity of the wild type cytokine, more preferably less than 40% of the biological activity of wild type cytokine, more preferably less than 30% of the biological activity of the wild type cytokine, more preferably less than 20% of the biological activity of the wild type cytokine, most preferably less than 10% of the biological activity of the wild type cytokine as compared to wild type cytokine that normally binds to the receptor. Preferably, the modified cytokine of the TNF superfamily is a mutant of the wild type cytokine of the TNF superfamily and the activity is compared with the wild type cytokine of the TNF superfamily. The affinity and/or the activity can be measured by any method known to the person skilled in the art. The affinity of the mutant TNF to the receptor, in comparison to the affinity of the wild type TNF to the receptor can be measured by Scatchard plot analysis and computer-fitting of binding data (e.g. Scatchard, 1949) or by reflectometric interference spectroscopy under flow through conditions, as described by Brecht et al. (1993).

Preferably, said cytokine is selected from the group, consisting of FasL, TRAIL, TNF, CD30L, CD40L, OX40L, RANKL, TWEAKL, LTalpha, LTbeta, LIGHT, CD27L, 41BBL, GITRL, APRIL, EDA, VEGI, and BAFF. Preferably, said cytokine is presented as a single chain, wherein the chains are connected by a linker sequence.

The modified cytokine is linked to a targeting moiety. "Linked" as used here may be by a covalent binding, or it may be by an affinity binding. In a non-limiting example, said targeting moiety may be a bispecific antibody, directed to a binding site on the target cell for one specificity, and to the modified cytokine, or to a tag fused to said cytokine for the other specificity. In another non-limiting example, the targeting moiety may be chemically linked to the modified cytokine, or it may be a recombinant fusion protein. Preferably, said targeting construct is a recombinant fusion protein. Preferably, said targeting moiety is targeting the cytokine to a tumor environment, particularly to the tumor vasculature (e.g. to endothelial cells of the tumor, typically neo-endothelial cells). Even more preferably, a targeting moiety is a binding molecule that can direct the fusion protein towards a binding site on a cell that is expressing a receptor for the cytokine of the TNF superfamily, preferably a receptor capable of interacting with the modified cytokine, by specific interaction between the binding site and the binding molecule. In one preferred embodiment, said binding molecule is a small compound, specifically binding to a molecule situated on the outside of the cell. In another preferred embodiment, said binding molecule is a sugar structure, directed towards a lectin-like molecule expressed on the cell wall. In another preferred embodiment said binding molecule is a peptide, targeting the tumor environment, preferably to the tumor vasculature. Such peptides are known to the person skilled in the art, and include, but are not limited to, NGR (targeting CD13 isoforms expressed in tumor vessels) and RGD peptides (Yang et al., 2011; WO2005054293). Preferably, said peptide is an RGD-4C peptide (Arap et al., 1998) which targets the $\alpha_v\beta_3$ integrin. In still another preferred embodiment, said binding molecule is a protein comprising a binding domain. Binding domains are known to the person skilled in the art. Non-limiting examples of such binding domains are carbohydrate binding domains (CBD) (Blake et al, 2006), heavy chain antibodies (hcAb), single domain antibodies (sdAb), minibodies (Tramontano et al., 1994), the variable domain of camelid heavy chain antibodies (VHH), the variable domain of the new antigen receptors (VNAR), affibodies (Nygren et al., 2008), alphabodies (WO2010066740), designed ankyrin-repeat domains (DARPins) (Stumpp et al., 2008), anticalins (Skerra et al., 2008), knottins (Kolmar et al., 2008) and engineered CH2 domains (nanoantibodies; Dimitrov, 2009). Preferably, said targeting moiety is a nanobody.

In a preferred embodiment, the targeting moiety is linked to the modified cytokine in a recombinant fusion protein. The targeting moiety may be fused directly to the mutant cytokine, or it may be fused with the help of a linker fragment. Preferably, said linker is a GGS linker. Even more preferably, said linker consists of at least 5 GGS repeats, more preferably of at least 10 GGS repeats, more preferably of at least 15 GGS repeats, more preferably said linker is a linker consisting of 17-23 GGS repeats, most preferably said linker consists of 20 GGS repeats. The targeting moiety may be fused at the amino-terminal or at the carboxy-terminal end of the mutated cytokine; preferably said targeting moiety is fused at the amino-terminal extremity of the mutated cytokine molecule. Apart from the mutant cytokine and the targeting moiety, the construct may further comprise other domains such as, but not limited to, a tag sequence, a signal sequence, another cytokine or an antibody.

Preferably, the targeting moiety is directed towards a target selected from the group consisting of CD20, CD33, CD47, CD70, PSCA, PSMA, Her2, c-Met, EGFR, Axl, tenascin C, $\alpha_v\beta_3$ integrin, fibronectin EDA end EDB domains, fibronectin type III (FNIII) repeats (A1-D), tenascin-C, and CD13, and tumor cell-specific splice variants thereof. When the targeting moiety targets to the tumor vasculature, particularly envisaged targets include, but are not limited to, CD13, $\alpha_v\beta_3$ integrin, fibronectin EDA end EDB domains, fibronectin type III (FNIII) repeats (A1-D), and tenascin-C. According to alternative particular embodiments, said targeting moiety is directed to CD20. It is particularly envisaged that the targeting moiety is an antibody (or a nanobody), as antibodies against these targets are readily available and/or can easily be generated.

The mutation in the cytokine chain can be any mutation known to the person skilled in the art, such as a deletion, an insertion, or a point mutation. At least one chain has at least one mutation; however, several mutations may be combined in one chain. The three chains may carry the same mutations, or different mutations. Preferably said mutations are lowering the affinity of the cytokine to its receptor or one of its receptors. Preferably said mutation is a point mutation.

In one preferred embodiment, the cytokine is TNF, and the construct is targeted towards a marker, expressed on a TNFR1 and/or TNFR2 expressing cell. In another preferred embodiment, said marker is a tissue specific marker, even more preferably said marker is a neo-vasculature tissue or cancer tissue specific marker. Most preferably, said marker is selected from the group consisting of CD20, Her2, c-Met, EGFR, tenascin C, $\alpha_v\beta_3$ integrin, and CD13.

Preferably, the modified cytokine is a mutant TNF wherein the mutation is selected from the group consisting of mutations on position R32, N34, Q67, H73, L75, T77, S86, Y87, V91, I97, T105, P106, A109, P113, Y115, E127, N137, D143, A145. Even more preferably, said mutation is selected from the group consisting of TNF R32G, N34G, Q67G, H73G, L75G, L75A, L75S, T77A, S86G, Y87Q, Y87L, Y87A, Y87F, V91G, V91A, I97A, I97Q, I97S, T105G, P106G, A109Y, P113G, Y115G, Y115A, E127G, N137G, D143N, A145G and A145T. Even more preferably, said mutation is selected from the group consisting of Y87X, I97X and Y115X. Most preferably, said mutation is selected from the group consisting of TNF Y87Q, Y87F, I97A, I97S, Y115A and Y115G (numbering according to the human TNF sequence, genbank accession number BAG70306, version BAG70306.1 GI: 197692685, SEQ ID NO: 14). The mutation may be present in one, two or all three copies of the trimeric TNF. Different copies within the trimeric construct may carry different mutations; several mutations may be combined in one or more of the chains. Apart from the cited mutations, other mutations may be present in one or more chains.

Preferred regions for mutation in TRAIL are T127-R132, E144-R149, E155-H161, Y189-Y209, T214-1220, K224-A226, W231, E236-L239, E249-K251, T261-H264 and H270-E271 (Numbering based on the human sequence, genbank accession number NP_003801, version NP_003801.1, GI: 4507593).

Another aspect of the invention is a fusion protein according to the invention for use as a medicament. In one preferred embodiment, the fusion protein according to the invention is for use in treatment of cancer.

This is equivalent as stating that methods of treating cancer in a subject in need thereof are provided, comprising administering a fusion protein as described herein to said subject. The cancer is thereby treated. This can for instance be evaluated by evaluating tumor size, as shown in the Examples (see also FIG. 16).

Subjects suitable for treatment are typically mammals, most typically humans. However, treatment of non-human animals is also envisaged herein. Examples of non-human animals that can be treated include, but are not limited to, horses, cows, sheep, pigs, goats, cats, dogs, and other domesticated animals. If non-human animals are envisaged for treatment, it is particularly envisaged that the modified cytokine is from the species to be treated. Modifications by mutation are then modifications of the residues in homolog positions compared to the human sequence. By way of non-limiting example, as shown in the Examples section, in mouse TNF, the residue that is a homolog of Y87 in human TNF is at position 86 (Y86). This can be mutated as detailed above (e.g. Y86F or Y86Q).

Different forms of cancer can be treated using this strategy. Essentially, any tumor that can be targeted (directly or indirectly, through the tumor environment) with a targeting moiety, thereby reactivating the modified TNF family cytokine, and thus inducing tumor cell death, is suitable for treatment.

Particularly envisaged cancers thus are those that can be readily targeted. According to particular embodiments, the targeting is to the tumor vasculature. Accordingly, highly vascularized tumors are particularly envisaged. Examples of such tumors are those that can be treated with anti-angiogenic approaches, such as anti-VEGF drugs or anti-angiopoietin/Tie2 agents. These include, but are not limited to, breast cancer, renal cell carcinoma, colorectal cancer, non-small cell lung cancer (NSCLC), hepatocellular carcinoma, pancreatic cancer, glioblastoma, ovarian cancer, gastric cancer, prostate cancer, melanoma, gastrointestinal stromal tumor (GIST), neuroendocrine tumors, soft tissue sarcoma, medullary thyroid cancer, and endometrial cancer (see e.g. Welti et al., 2013, particularly Table 1 and Supplemental Table 1 therein).

According to particular embodiments, the cancer is a solid tumor. However, it should be noted that also hematological cancers such as leukemias (e.g. CML, AML), multiple myeloma and lymphomas can be treated with anti-angiogenic agents (Schmidt and Carmeliet, 2011; Roccaro et al., 2006). Thus, according to alternative embodiments, the cancer is a tumor of the hematopoietic and/or lymphoid tissues (see also Example 12).

As angiogenesis plays a major role in tumor metastasis, and in activating metastatic lestions, according to particular embodiments, the cancer is a metastatic cancer. The increased presence of neo-endothelial cells will make these cancers more susceptible to molecules targeted to markers of these cells (the tumor vasculature markers described above).

EXAMPLES

Materials and Methods to the Examples
Nanobodies

Figure 7:
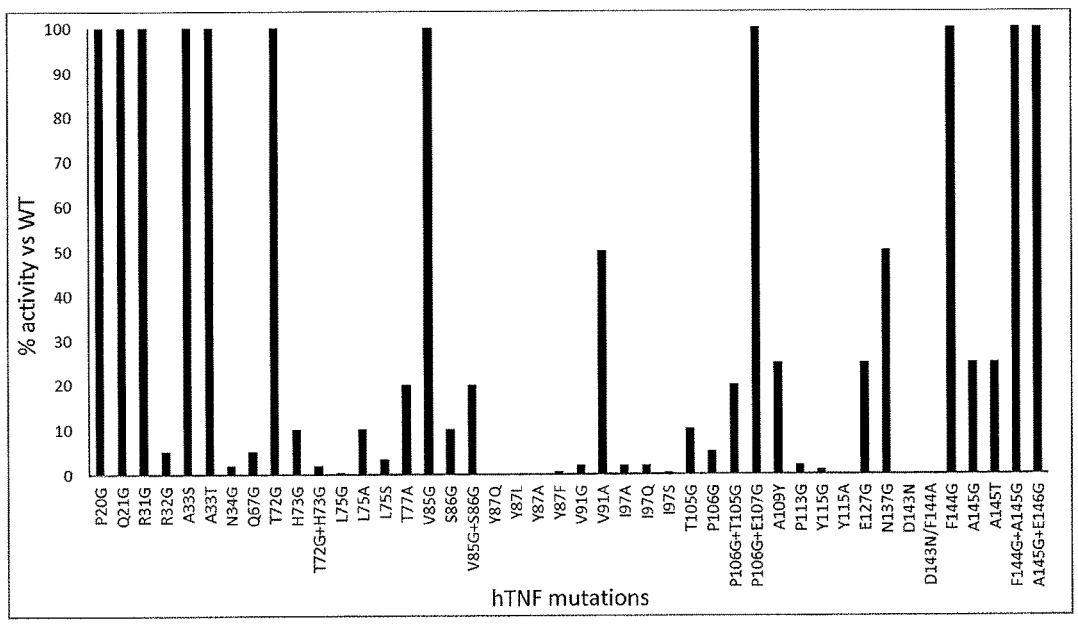
FIG. 7: % activity of hTNF mutants compared to WT hTNF as measured by toxicity on MCF7 cells (a breast cancer cell line).

The nanobody 4-10 directed against the murine leptin receptor (mLR) was described in Zabeau et al. (2012). Its coding sequence is cloned into the mammalian expression vector pMET7 (Takebe et al., 1988) in fusion with the SIgK leader peptide, the HA tag and albumin. Plasmid name: pMET7 S1gK-HA-4.11-Albumin. The anti-Her2 nanobody 1R59B was described in Vaneycken et al. (2011). The NB 2HCD25 directed against the human CD20 (hCD20) and the 2MC57 NB against mouse CD20 (mCD20) were generated using standard techniques (Gharouhdi et al., 1997; Pardon et al., 2014). The control NB BclI10 was described in De Groeve et al. (2010).

scTNF scTNF that consists of three hTNF monomers coupled via GGGGS-linkers (SEQ ID NO: 1) has been described by Boschert et al. (2010). The Y87Q mutation in hTNF was shown to completely abrogate the binding to both receptors, TNF-R1 and TNF-R2. Mutating 197 results in reduced binding of hTNF to both receptors (Loetscher et al., 1993). A whole range of residues within hTNF were mutated (QuikChange Site-Directed Mutagenesis Kit, Stratagene Cat#200518) and tested for their toxic effects on MCF7 cells (FIG. 7). We selected the following mutations for the targeted constructs: Y87Q, Y87F, I97S, I97A, Y115A, Y115G. The coding sequences of sc hTNF WT-6xGGS, sc hTNF Y87Q3x-6xGGS, sc hTNF I97A3x-6xGGS, sc hTNF Y87Q1xI97A2x-6xGGS, sc hTNF Y87Q2x I97A1x-6xGGS, sc hTNF WT1 x Y87Q2x-6xGGS, sc hTNF WT2x Y87Q1x-6xGGS, sc hTNF I97S3x-6xGGS, sc hTNF Y115A3x-6xGGS, sc hTNF Y87F3x, sc hTNF Y115G3x, sc mTNF WT and sc mTNF Y86F3x were generated by gene synthesis (GeneArt). The individual chains are separated by a GGGGS (SEQ ID NO: 1) linker.

scTNF-nanobody Fusion Construction

The coding sequence of the 1R59B Her2 nanobody was synthesized by PCR from the plasmid pHEN6-1R59B with the following primers:

```
forward
                                            (SEQ ID NO: 2)
5'-GTCAAGATCTGGCGGTTCGGCGGCCGCAATGGCCCAGGTGCAGCTGC
AG-3', reverse
                                            (SEQ ID NO: 3)
5'-CAGTTCTAGATTACTTATCGTCGTCATCCTTGTAATCCGAACCGCCG
TCCGGAGAGGAGACGGTGAC-3'.
```

This PCR introduces a GGS in between a BglII and NotI site at the amino terminus and a FLAG tag at the carboxy terminus of the 1R59B nanobody. The PCR product was digested with BglII and XbaI. The pMK-RQ-sc hTNF WT, pMK-RQ-sc hTNF Y87Q3x and pMK-RQ-sc hTNF I97A3x were digested with NdeI and BglII. The digested PCR product and synthetic gene fragments were cloned into NdeI-XbaI digested pMET7 SIgK-HA-leptin vector to obtain pMET7 SIgK-HA-sc hTNF WT-6xGGS-1R59B-FLAG, pMET7 SIgK-HA-sc hTNF Y87Q3x-6xGGS-1R59B-FLAG and pMET7 SIgK-HA-sc hTNF I97A3x-6xGGS-1R59B-FLAG. The control vectors without the 1R59B nanobody were obtained by inserting the following annealed oligos containing the GGS and the FLAG tag in between BglII and XbaI instead of the PCR product:

```
forward:
                                            (SEQ ID NO: 4)
5' GATCTGGCGGTTCGGCGGCCGCAGATTACAAGGATGACGACGATAAG
TAAT 3', reverse:
                                            (SEQ ID NO: 5)
5'CTAGATTACTTATCGTCGTCATCCTTGTAATCTGCGGCCGCCGAACCG
CCA3'.
```

The control vector with only the 1R59B nanobody was obtained by inserting the following annealed oligos instead of the NdeI-sc hTNF-BglII fragment: forward: 5'-TATGAT-GTGCCCGACTACGCTGGCGGCAGCA-3' (SEQ ID NO: 6), reverse 5'-GATCTGCTGCCGCCAGCG-TAGTCGGGCACATCA-3' (SEQ ID NO: 7). The length of the GGS linker was adjusted to a GGS linker of 13 repeats and 19 repeats by adding 7xGGS or 13xGGS repeats (made by gene synthesis, GeneArt) to the original 6xGGS in between the BglII and NotI site.

A similar approach was used to obtain pMET7 SIgK-HA-sc hTNF WT-6x/13x/19xGGS-4.10-FLAG, pMET7 SIgK-HA-sc hTNF Y87Q3x-6xGGS-4.10-FLAG, pMET7 SIgK-HA-sc hTNF I97A3x-6x/13x/19xGGS-4.10-FLAG, pMET7 SIgK-HA-sc hTNF Y87Q1x 197A2x-6x/13x/19xGGS-4.10-

FLAG, pMET7 SIgK-HA-sc hTNF Y87Q2x I97A1x-6x/13x/19xGGS-4.10-FLAG, pMET7 SIgK-HA-sc hTNF WT-6x/13x/19xGGS-2HCD25-FLAG, pMET7 SIgK-HA-sc hTNF I97S3x-6x/13x/19xGGS-2HCD25-FLAG, pMET7 SIgK-HA-sc hTNF I97A3x-6x/13x/19xGGS-2HCD25-FLAG and pMET7 SIgK-HA-sc hTNF Y115A3x-6x/13x/19xGGS-2HCD25-FLAG.

To obtain the individual trimerizing hTNF constructs, sc hTNF in pMet7-SIgK-HA-sc hTNF WT-GGS-4.10-Flag was replaced by NdeI-SalI digest of the PCR product obtained with the forward 5'-CATATGATGTGCCCGAC-TACGCTGGCGGCAGCAGCTCTAGAACCCCCAGC-GATAAGCCTGTG-3' (SEQ ID NO: 8) and the reverse primer 5'-GTCGACCAGGGCAATGATGCCGAAGT-3' (SEQ ID NO: 9) on the plasmids pMet7-SIgK-His-hTNF WT or pMet7-SIgK-His-hTNF I97A. This resulted in the following vectors: pMet7-SIgK-HA-hTNF WT-6xGGS-4.10-Flag and pMet7-SIgK-HA-hTNFI97A-6xGGS-4.10-Flag.

The nanobody-TNF fusion expression constructs with the NB N-terminally of individual trimerizing or single chain, human or mouse TNF were made in pMet7 and designed as such that each subunit is interchangeable through unique restriction sites: AgeI-nanobody-SalI-GGS linker-NotI-TNF-XhoI-His-XbaI.

pGL3-(IL6-κB)3-fireflyluciferase was kindly provided by W. Vanden Berghe (Vanden Berghe et al., 1998).

Production of the Nanobody-TNF Fusion Proteins for in vitro Studies

HekT cells were transfected with the protein fusion constructs using the standard calcium phosphate precipitation method. 48 hours after the transfection culture mediums were harvested and stored at −20° C. The concentration was determined with a commercial hTNF ELISA (DY210, R1D systems).

Production of the Nanobody-scTNF Fusion Proteins for in vivo Studies

FreeStyle™ 293-F cells were transfected with the protein fusion constructs using the PEIpro™ transfection reagent (PolyPlus, Cat#115-375) according to the manufacturer's guidelines. The endotoxin content was in all preparations under the detection limit as assessed by a chromogenic Limulus Amebocyte Lysate Assay (Lonza, Cat#50-647U).

Cell Lines

Hek, HekT, Hek-mLR, MCF7, MCF7-hCD20, MCF7-mLR and B16BI6-mCD20 cells were grown in DMEM supplemented with 10% FCS. The FreeStyle™ 293-F cell line was obtained from Invitrogen, Life Technologies (Cat# R790-07) and maintained in FreeStyle™ 293 Expression Medium from Gibco, Life Technologies (Cat#12338). The human breast cancer SK-BR-3 (ATCC: HTB-30) cell line was obtained from ATCC and maintained in McCoy's 5A medium supplemented with 10% FCS.

The Hek-mLR cell line was generated as follows: Flp-In-293 cells (Invitrogen) were stably co-transfected with a plasmid containing the expression cassettes for mEcoR and neomycin resistance and with a pXP2d2-rPAP1-luci reporter construct (Eyckerman et al. 2001). Stable transfected clones were isolated in G418 (400 ug/ml)-containing medium and a clone was selected with high LIF (1 ng/ml)-induced luciferase activity. The expression vector pcDNA5/FRT containing the mLR was stably integrated in this cell line using the Flp-In recombinase reaction (Invitrogen) and after selection on hygromycin (100 μg/ml) for 10 days.

The human breast cancer MCF7 (ATCC: HTB-22) cell line was obtained from ATCC. The MCF7-hCD20 and MCF7-mLR cell lines were generated as follows: MCF7 cells were stably co-transfected with a plasmid containing the expression cassette for hCD20 or mLR, and with a plasmid containing the neomycin resistance gene. Stable transfected cells were selected with G418 (1 mg/ml)-containing medium, followed by FACS sorting of hCD20- or mLR-expressing cells.

The B16BI6-mCD20 cell line was generated as follows: B16B16 cells were stably co-transfected with a plasmid containing the expression cassette for mCD20 and with a plasmid containing the neomycin resistance gene. Stable transfected cells were selected with G418 (2 mg/ml)-containing medium.

The human breast cancer SK-BR-3 (ATCC: HTB-30) cell line was obtained from ATCC and maintained in McCoy's 5A medium supplemented with 10% FCS.

Measurement of the Luciferase Activities

TNF specific activities were measured by quantifying the luciferase activity under the control of the NF-κB promoter. Two days after transfection of the NF-κB luciferase reporter (pGL3-(IL6-κB)3-fireflyluciferase) by standard calcium phosphate precipitation method, cells were stimulated for 6h with targeted or control sc hTNF. Lysates were prepared (lysis buffer: 25 mM Tris, pH 7.8, 2 mM EDTA, 2 mM dithiothreitol, 10% glycerol, 1% Triton X-100), and 35 μl of luciferase substrate buffer (20 mM Tricine, 1.07 mM $(MgCO_3)_4Mg(OH)_2.5H_2O$, 2.67 mM $MgSO_4.7H_2O$, 0.1 mM EDTA, 33.3 mM dithiothreitol, 270 μM coenzyme A, 470 μM luciferin, 530 μM ATP, final pH 7.8) was added per 50 μl of lysate. Light emission was measured for 5 s in a TopCount chemiluminescence counter (Packard).

Quantitative RT-PCR

The expression of the TNF inducible gene IL-6 was quantified by RT-PCR relatively to HPRT in SK-BR-3 cells treated for 6 hours with 500 ng/ml of targeted or control sc hTNF. Total RNA was purified with RNeasy columns (Qiagen) and equal amounts of RNA (0.5 μg) were used for reverse transcription using the Primescript RT Reagent kit (Takara Bio, Shiga, Japan), following the manufacturer's instructions. The 10-fold diluted cDNA was added to an RT-QPCR mixture containing 1xSYBR Green I master mix (04 887 352 001, Roche) and 1 nM gene-specific primers. Assays were performed in triplicate on a LightCycler 480 Real-Time PCR System thermocycler (Roche Applied Science), and the results were analyzed using the AACT method. The following primers were used:

```
                                         (SEQ ID NO: 10)
HPRT forward: 5'TGACACTGGCAAAACAATGCA3';

(SEQ ID NO: 11)
HPRT reverse: 5'GGTCCTTTTCACCAGCAAGCT3';

(SEQ ID NO: 12)
IL-6 forward: 5'GACAGCCACTCACCTCTTCA3';

(SEQ ID NO: 13)
IL-6 reverse: 5'AGTGCCTCTTTGCTGCTTTC3'.
```

Toxicity Analysis on MCF7 Cells

TNF-specific activities were also measured by assessing the cellular toxicity on MCF7 cells. 1000 cells were plated in a black 96-well plate and 24 hours later stimulated with the different TNF constructs. After 48-72 hours, the number of viable cells was determined using the CellTiter-Glo Luminescent Cell Viability Assay (Promega Cat# G7570) according to the manufacturer's guidelines.

In vivo Toxicity Analysis

To assess hTNF toxicity in vivo, female 8 weeks old C57BL/6J mice (purchased from Charles River, France) were injected intraperitoneally with 500 ng rhTNF or sc hTNF-nanobody fusion proteins in combination with 10 mg D-Galactosamine (diluted in LPS-free PBS, injected in a volume of 500 µl). Morbidity was monitored by measurement of peripheral (rectal) body temperature. n=2-4 per fusion protein.

To evaluate mTNF toxicity in vivo, mice were injected intravenously with 10, 35, 100 or 200 µg sc mTNF-nanobody fusion proteins (injected volume 200 µl, dilution in LPS-free PBS). Morbidity was monitored by measurement of peripheral (rectal) body temperature. n=2 per dose, per fusion protein, except for 200 µFg (n=1).

In vivo Anti-tumor Studies

Female C57BL/6J mice of 8 weeks old were shaved and inoculated with 6×10$^5$ B16BI6-mCD20 tumor cells subcutaneously in the back (day 0). Treatment was started when the product of the largest perpendicular diameters was approximately 50 mm$^2$ (on day 10). PBS or 35 µg nanobody-sc mTNF fusion proteins were administered for 8 consecutive days (day 10-17, indicated in FIG. 16A as a grey bar) via paralesional injection (subcutaneous injection near the tumor site but outside the tumor nodule). Tumors were measured daily with a caliper and are shown as mean±SEM. Morbidity was monitored by daily measurement of body weight and temperature. n=5 per treatment.

Example 1

The sc hTNF-nanobody Fusion Proteins

Figure 1:
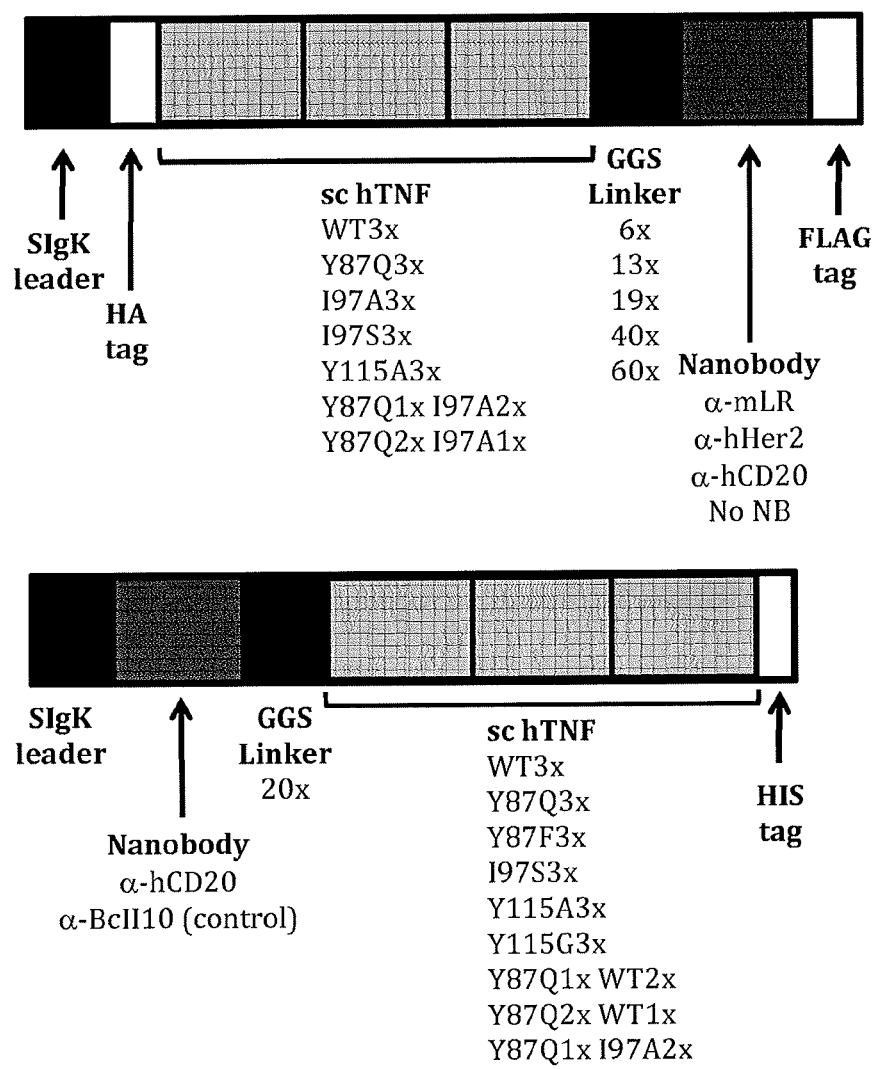
FIG. 1: Representation of the structural elements of the different set-ups of the sc hTNF-nanobody fusion protein.

FIG. 1 shows a schematic representation of the sc hTNF-nanobody fusion proteins either with the nanobody N- or C-terminally of sc hTNF.

Example 2

Targeting TNF Activity on mLR-expressing Hek Cells

Figure 2:
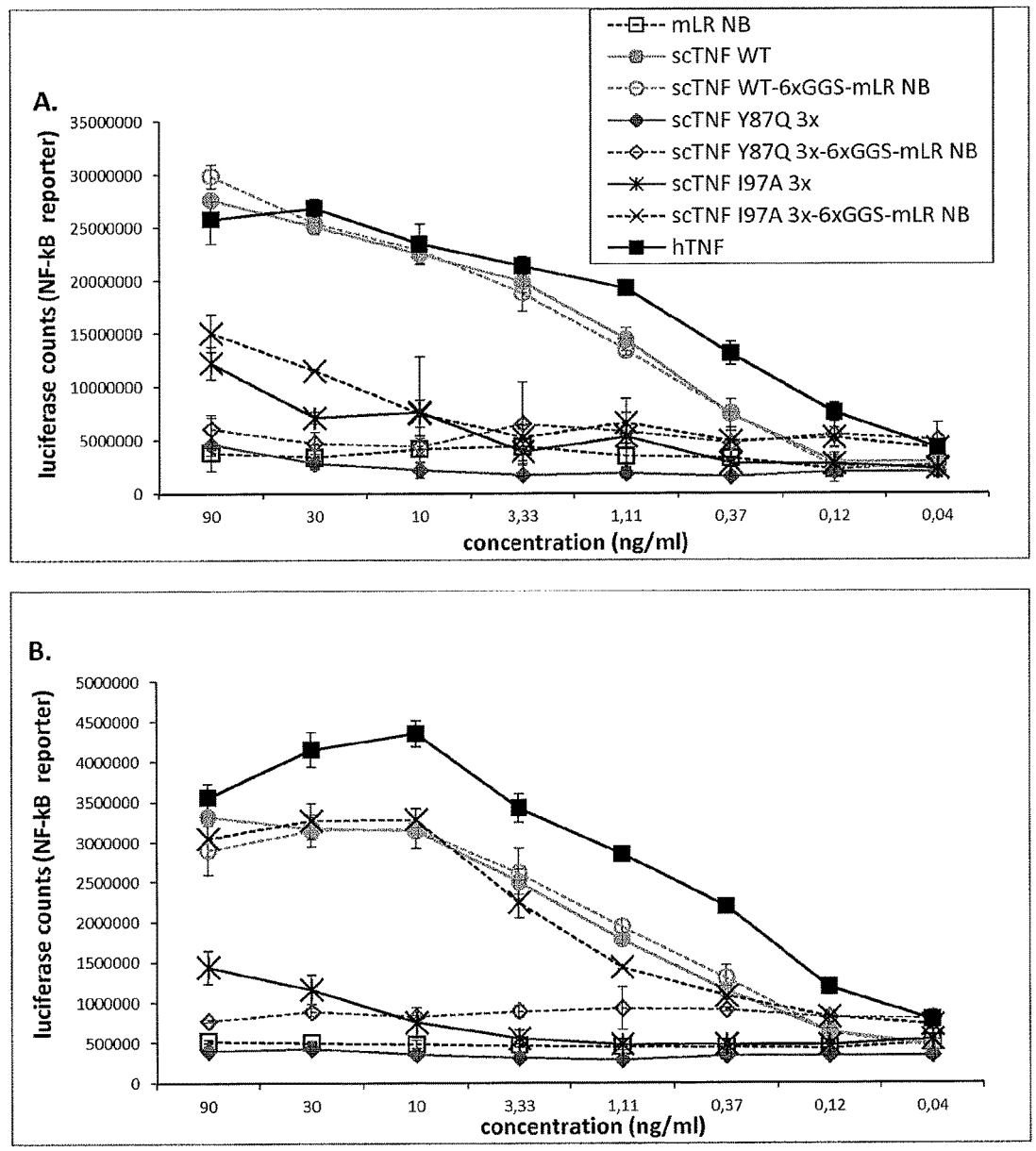
FIG. 2: Firefly luciferase activity induced by the indicated sc hTNF preparations, as compared to WT hTNF, on HekT cells (panel A) or Hek-mLR cells (panel B). Both were transiently transfected with the NF-KB luciferase reporter.

The induction of NF-κB luciferase reporter activity upon TNF stimulation was tested in HekT cells and in Hek cells that express the murine leptin receptor (Hek-mLR). As shown in FIG. 2A, WT sc hTNF-induced NF-KB induction is completely (>1000-fold) or partly (100-fold) abrogated by the Y87Q3x or the I97A3x mutation, respectively. Moreover, in HekT cells that do not express the mLR, all sc hTNF constructs (WT, Y87Q3x and I97A3x) induce similar NF-κB activity independently of the fusion to the mLR nanobody (FIG. 2A). In contrast, coupling to the mLR nanobody is able to restore NF-κB induction of sc hTNF I97A3x in Hek cells that express the mLR to a similar extent as WT sc hTNF (FIG. 2B). We estimated that cells expressing the mLR are 100-fold more sensitive than parental HekT cells to the nanobody-coupled sc hTNF I97A3x. In contrast, the triple Y87Q mutation did not show any rescue effect of TNF responsiveness in Hek-mLR cells compared to HekT cells (FIG. 2B).

Example 3

Comparison of Different Mutant Combinations and Different Linker Lengths

Figure 3:
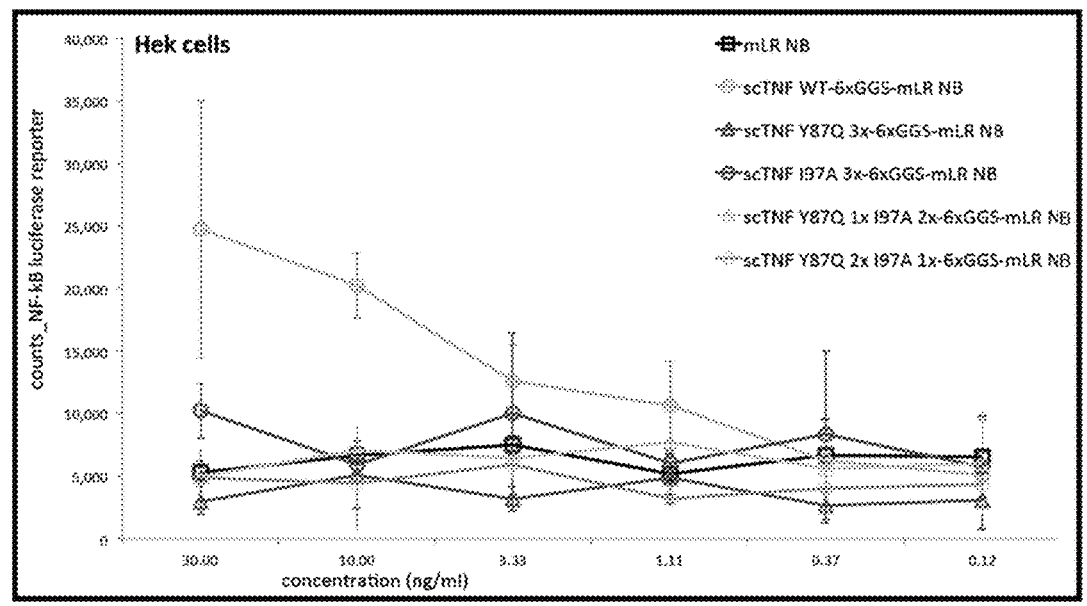
FIG. 3: Firefly luciferase activity induced by the indicated sc hTNF preparations carrying a linker with 6 GGS repeats on HekT cells (panel A) or Hek-mLR cells (panel B). Both were transiently transfected with the NF-KB luciferase reporter.
Figure 3:
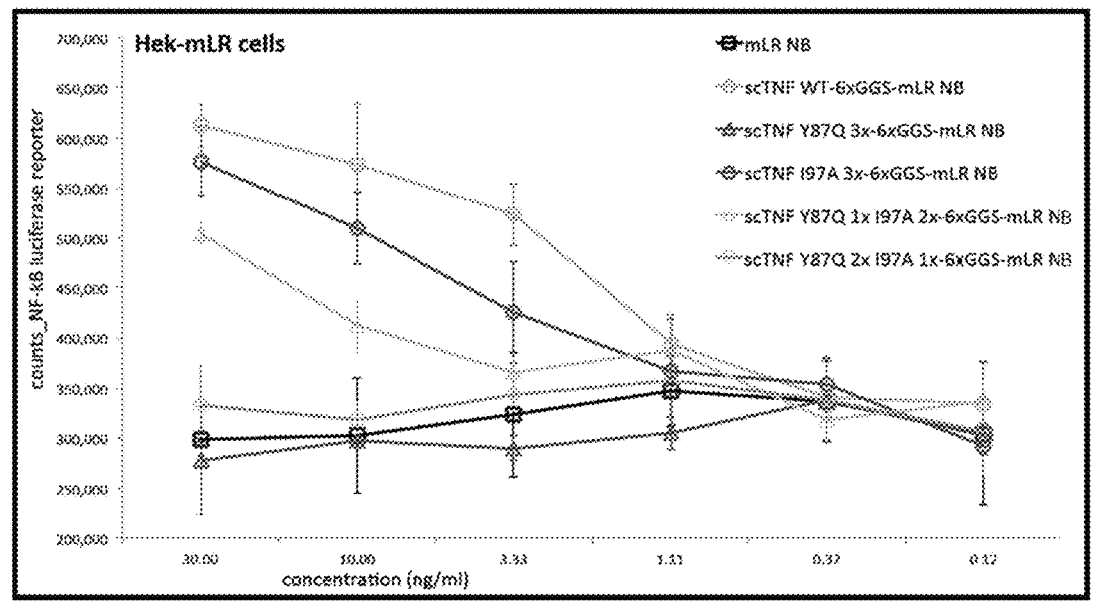
Figure 4:
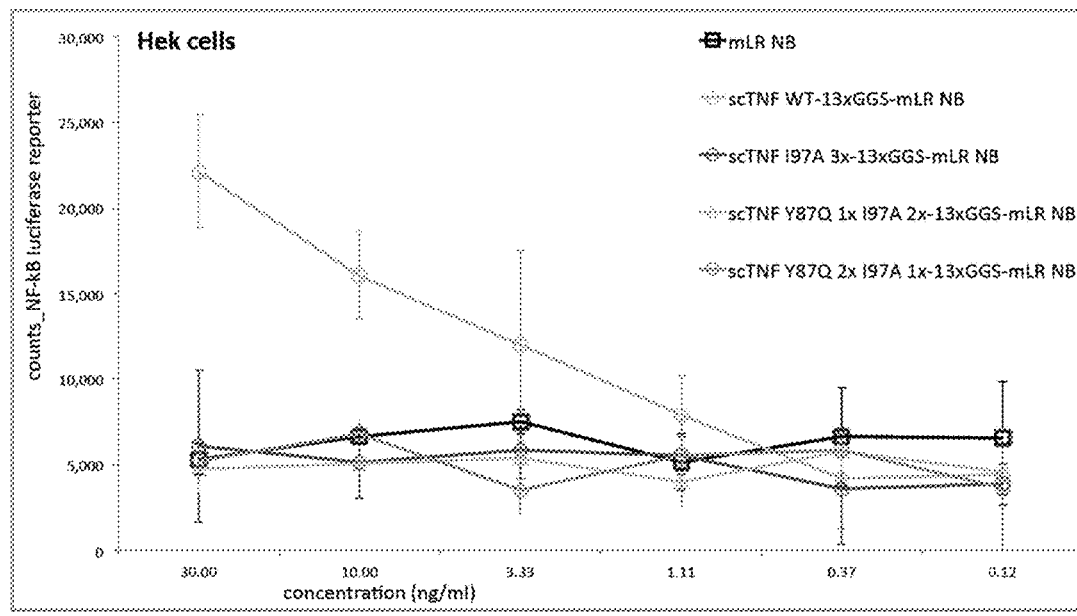
FIG. 4: Firefly luciferase activity induced by the indicated sc hTNF preparations carrying a linker with 13 GGS repeats on HekT cells (panel A) or Hek-mLR cells (panel B). Both were transiently transfected with the NF-KB luciferase reporter.
Figure 4:
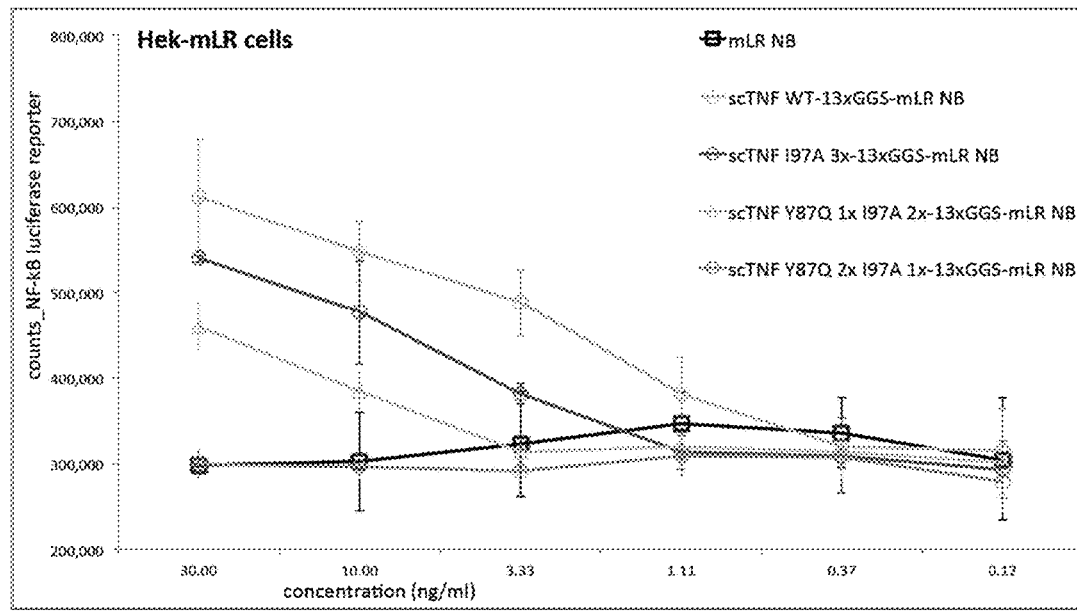
Figure 5:
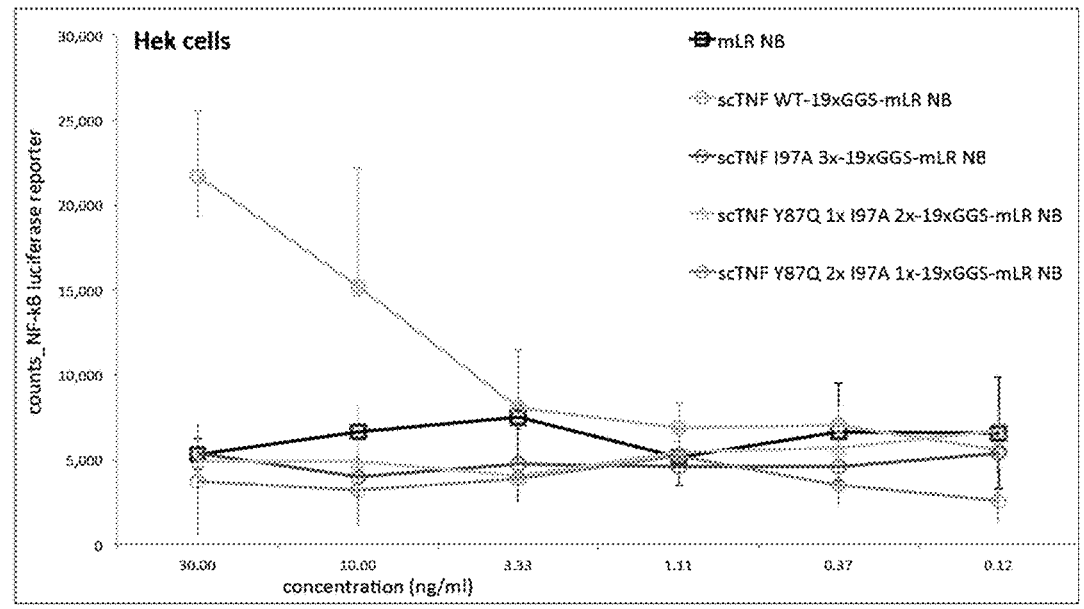
FIG. 5: Firefly luciferase activity induced by the indicated sc hTNF preparations carrying a linker with 19 GGS repeats on HekT cells (panel A) or Hek-mLR cells (panel B). Both were transiently transfected with the NF-κB luciferase reporter.
Figure 5:
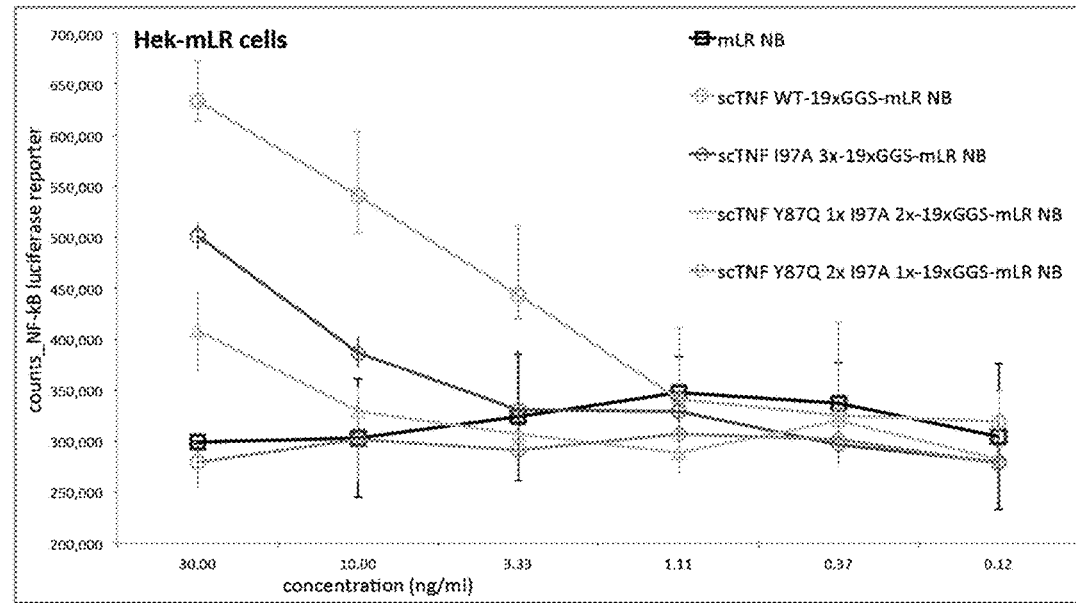

In order to optimize the constructs, sc hTNF constructs with different mutations in the individual chains were tested, as well as different linker lengths between the sc hTNF and the targeting moiety. The results are summarized in FIGS. 3, 4 and 5. sc hTNF I97A3x and sc hTNF Y87Q1x I97A2x do not show activity on Hek cells that do not express the leptin receptor, but have a clear dose dependent activity when targeted to the leptin receptor.

Example 4

Targeting TNF Activity on Her2-expressing Hek Cells

We generated fusions protein using the α-Her2 nanobody 1 R59B and sc hTNF WT, sc hTNF Y87Q3x or sc hTNF I97A3x. The linker between the nanobody and sc hTNF was either 6xGGS or 19xGGS. These molecules were tested on the Her2-overexpressing SK-BR-3 breast cancer cell line for the induction of the IL-6 TNF-inducible gene as determined relatively to HPRT by quantitative RT-PCR.

Figure 6:
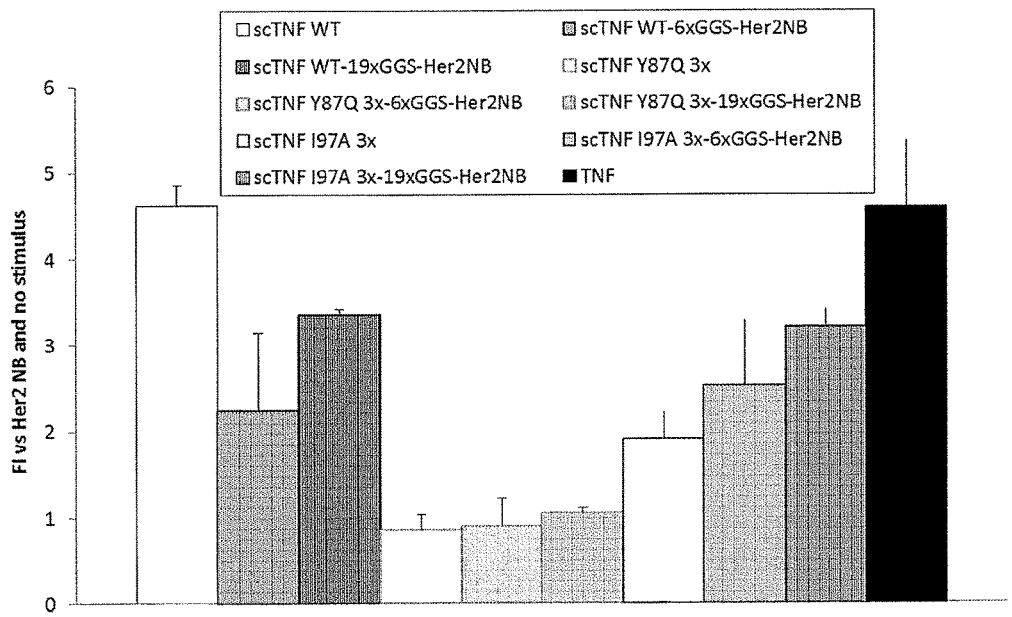
FIG. 6: Fold induction of IL-6 mRNA levels upon treatment of SK-BR-3 cells with 500 ng/ml of the indicated sc hTNF preparations compared to the levels in untreated cells and cells stimulated with the Her2 nanobody. Data represents the mean±SD of 2 independent experiments (n=4).

FIG. 6 shows the fold induction of IL-6 mRNA upon sc hTNF treatment (500 ng/ml) compared to IL-6 mRNA levels in untreated cells and cells stimulated with the Her2 nanobody. In correspondence to the transcriptional activation of NF-κB, we observe that Y87Q3x mutation completely prevents TNF-induced IL-6 production while sc hTNF I97A3x can still induce IL-6 production but to a lesser extent than WT sc hTNF. When sc hTNF is fused to the nanobody less IL-6 mRNA is produced. This could be due to steric hindrance as the effect is more pronounced with the 6xGGS linker compared to the longer 19xGGS linker where there is likely more flexibility. By coupling sc hTNF I97A3x to the Her2 nanobody the induction of IL-6 can be restored to similar levels as WT sc hTNF coupled to the nanobody through the corresponding linker. In contrast, specific targeting of the more severe Y87Q3x sc hTNF mutant to Her2-expressing cells cannot restore the IL-6 inducing property of sc hTNF.

Example 5

Comparing the Toxicity of hTNF Mutants on MCF7 Cells

Because of the relatively high residual activity of I97A3x mutant sc hTNF, we searched for further mutations by measuring the toxicity of different individual trimerizing hTNF mutants as luciferase activity in MCF7 cells. The activity of the mutants relative to WT individual trimerizing TNF is shown in FIG. 7. Most mutations do not affect the TNF activity drastically (>1% of WT) and might be less promising for the development of targeted constructs because of their possibly remaining substantial toxicity. We are more interested in mutations that (almost) completely abrogate TNF function. The use of null mutations (<0.1% of WT) results in targeted constructs that do not have side effects but that have as a possible drawback that reactivation upon targeting is less easily accomplished. The mutations that have some residual activity (0.02-5% of WT, particularly 0.1%-1% of WT) have a better chance of being reactivated whilst not being toxic. 6 different mutations covering an activity range between 0.02 and 5% of individual trimerizing WT TNF were selected for the development of the targeted modified cytokines: Y87Q (0.02%), I97S and Y115A (0.2%), Y87F (0.5-1%), Y115G (1-2%) and I97A (2-5%).

Example 6

Targeting TNF Activity on mLR-expressing MCF7 Cells

Figure 8:
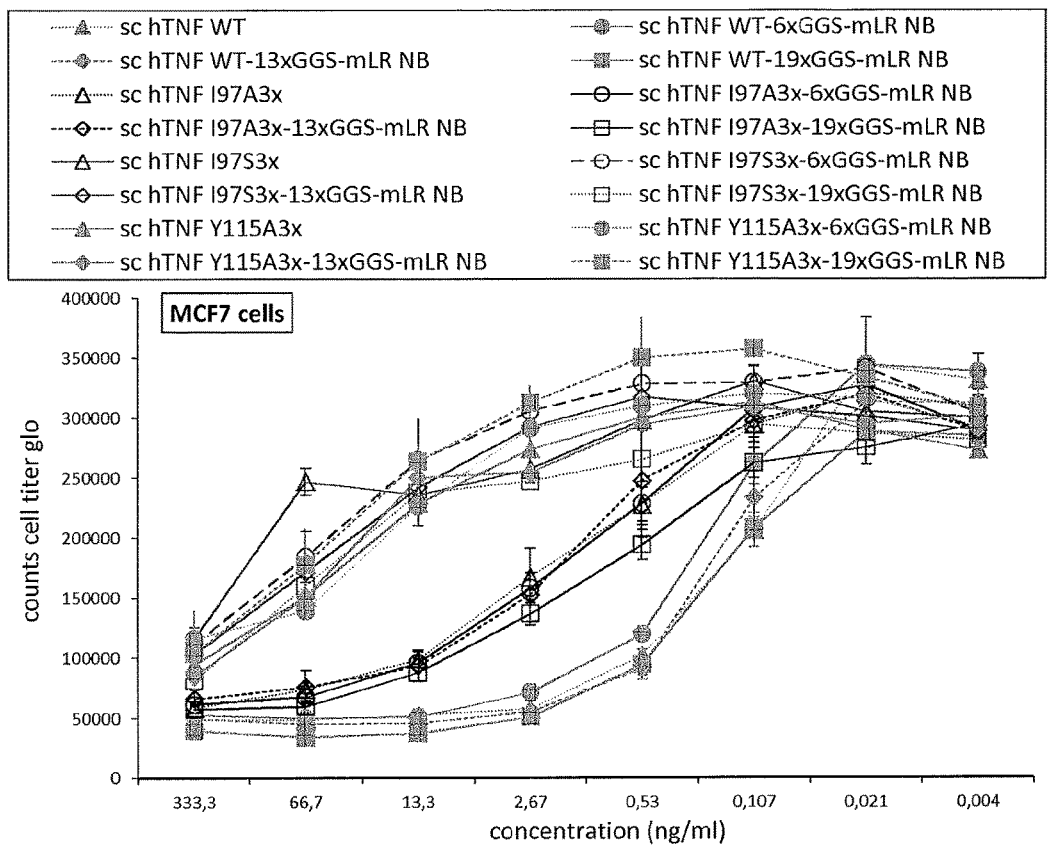
FIG. 8: Toxicity on MCF7 (panel A) or MCF7-mLR (panel B) cells of targeted modified TNFs coupled to mLR NB (NB C-terminally of TNF).
Figure 8:
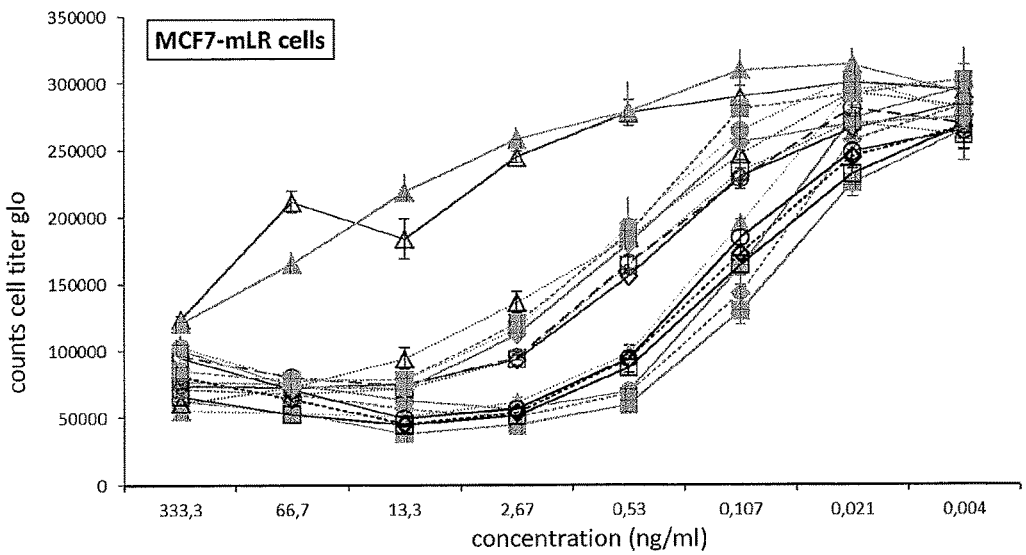

The toxicity of mLR NB-targeted TNF was assessed on MCF7 and MCF7-mLR cells. Different mutations (I97A3x, I97S3x and Y115A3x) were tested as well as different linkers between sc hTNF and the mLR NB (6xGGS, 13xGGS, 19xGGS). As shown in FIG. 8A, toxicity is reduced 20-fold by the I97A3x mutation and 500-fold by the I97S3x and Y115A3x mutation, which is similar to what we observed for individual trimerizing TNF (FIG. 7). Moreover, in MCF7 cells that do not express the mLR, fusion to the mLR NB does not alter the activity of WT or mutant sc hTNF (FIG. 8A), while this fusion reactivates all sc hTNF mutants on MCF7-mLR cells (FIG. 8B). We estimated that cells expressing the mLR are 100-fold more sensitive than parental MCF7 cells to the NB-coupled I97S3x and Y115A3x sc hTNF. However, these targeted modified TNFs are still about 20-fold less active than WT sc hTNF. In contrast, the I97A3x targeted modified TNF is restored to WT activity levels on MCF7-mLR cells, which corresponds to a 20-fold reactivation (FIG. 8B).

Example 7

Targeting TNF Activity on hCD20-expressing MCF7 Cells

Figure 9:
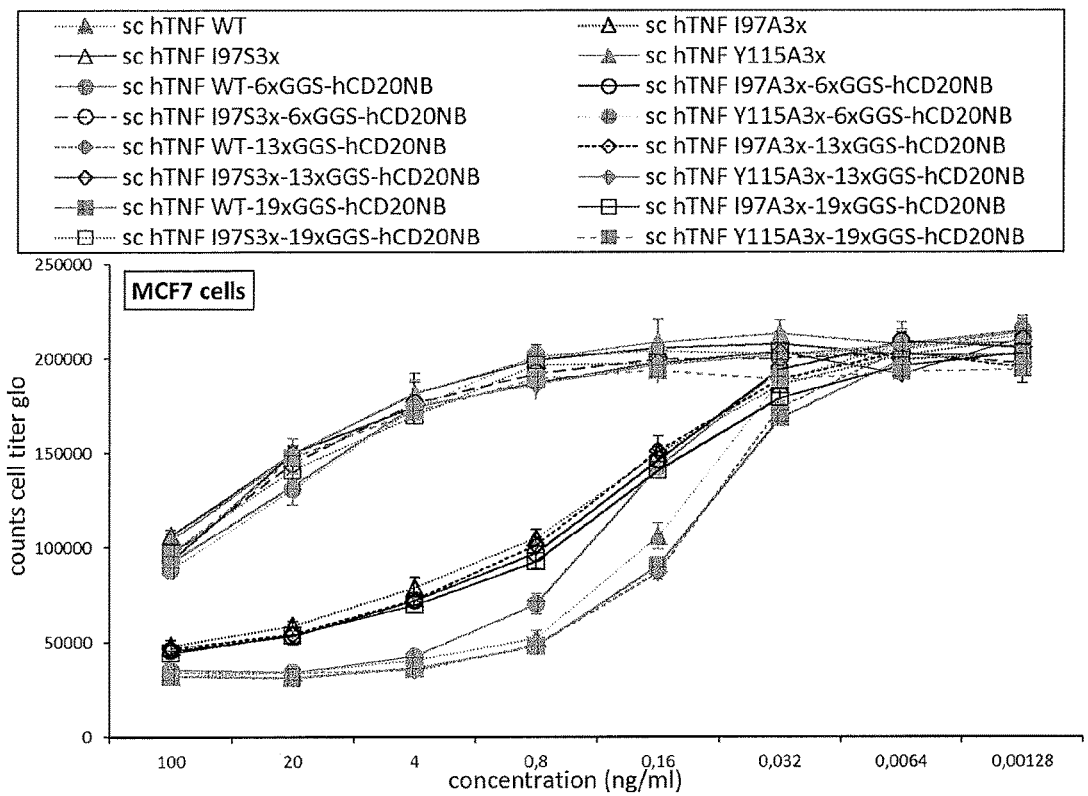
FIG. 9 Toxicity on MCF7 (panel A) or MCF7-hCD20 (panel B) cells of targeted modified TNFs coupled to hCD20 NB (NB C-terminally of TNF).
Figure 9:
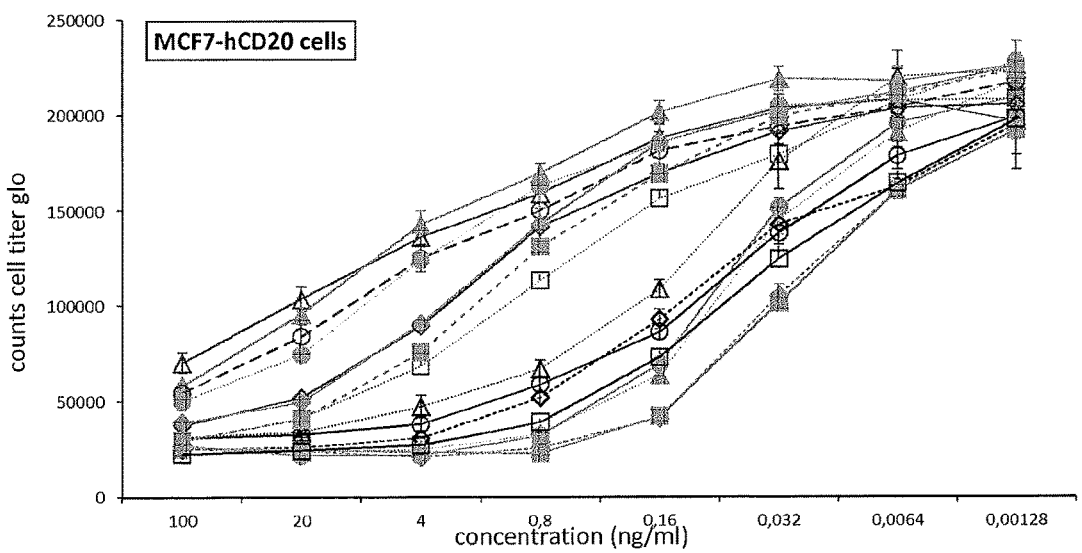

To assess the effect of other targeting moieties for the targeting of modified TNF, we replaced the mLR NB in the constructs of Example 6 with the hCD20 NB and tested their toxicity on MCF7 cells and MCF7 cells that express hCD20 (MCF7-hCD20). The results are shown in FIG. 9. As expected, mLR NB and hCD20 NB targeted modified TNFs behave similarly on parental MCF7 cells (FIGS. 8A & 9A).

Example 8

Figure 10:
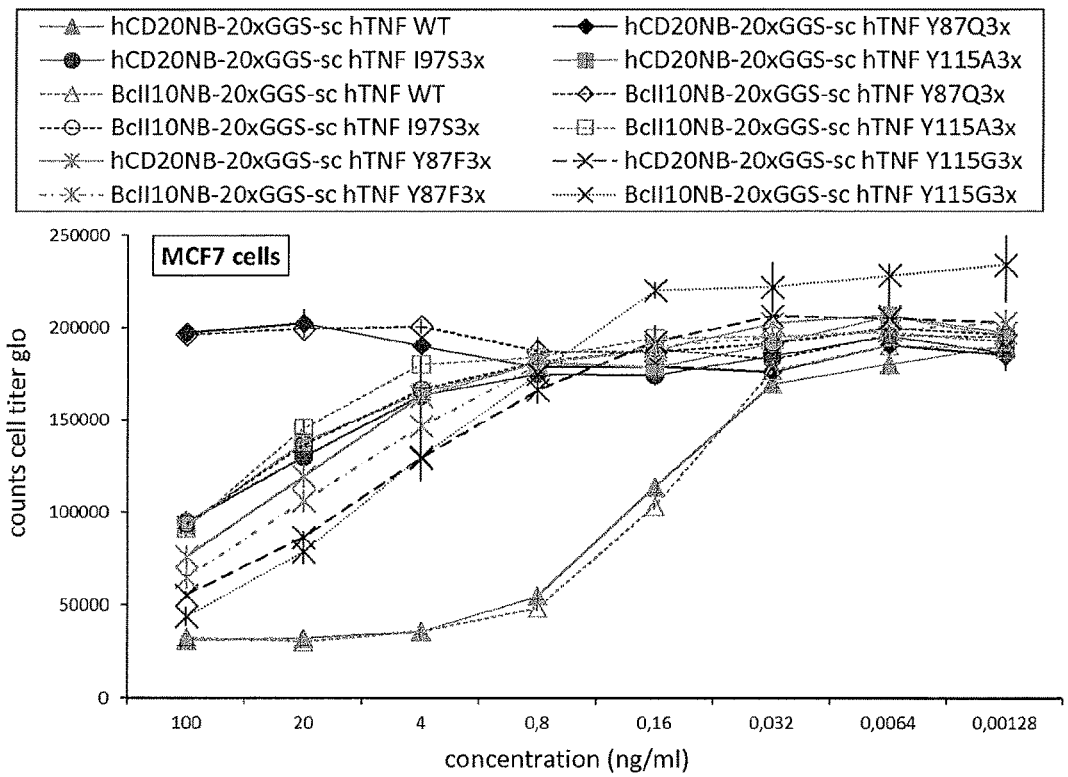
FIG. 10: Toxicity on MCF7 (panel A) or MCF7-hCD20 (panel B) cells of targeted modified TNFs coupled to hCD20 or control BclI 10 NB (NB N-terminally of TNF).
Figure 10:
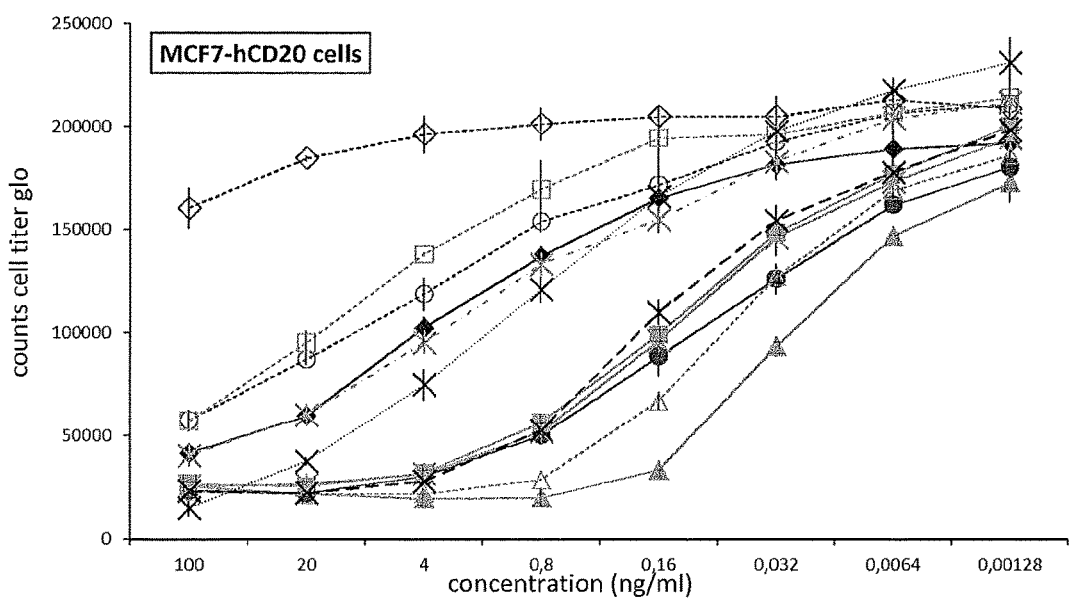

Targeting TNF Activity on hCD20-expressing Cells with a Different hCD20 NB Fusion Set-up We tried to improve the hCD20 NB-TNF constructs by placing the NB in front instead of after sc hTNF. We also tested 2 additional, less drastic mutations (Y87F3x and Y115G3x, FIG. 7). The MCF7 and MCF7-hCD20 toxicity studies with these constructs are shown in FIG. 10. Sc hTNF coupled to hCD20 NB exerts the same toxicity on MCF7 cells as the corresponding mutant coupled to the control Bcl10 NB (FIG. 10A), and the level of activity is similar as to what we observed for the individual trimerizing TNF mutants (FIG. 7). This reduced toxicity of the mutants is (partially) reverted upon hCD20 targeting on the MCF7-hCD20 cells: hCD20 NB-coupled modified TNF give a 10-fold (Y115G3x), 15-fold (Y87F3x), 100-fold (I97S3x, Y115A3x) or even higher (Y87Q3x) increased activity compared to the corresponding Bcl10 control NB-coupled sc hTNFs (FIG. 10B). In this experiment, when the hCD20 NB is placed at the carboxy-terminal end instead of the amino-terminal end of the sc hTNF the reactivation is less (FIG. 9B).

Example 9

Comparison of Different Mutant Combinations

Figure 11:
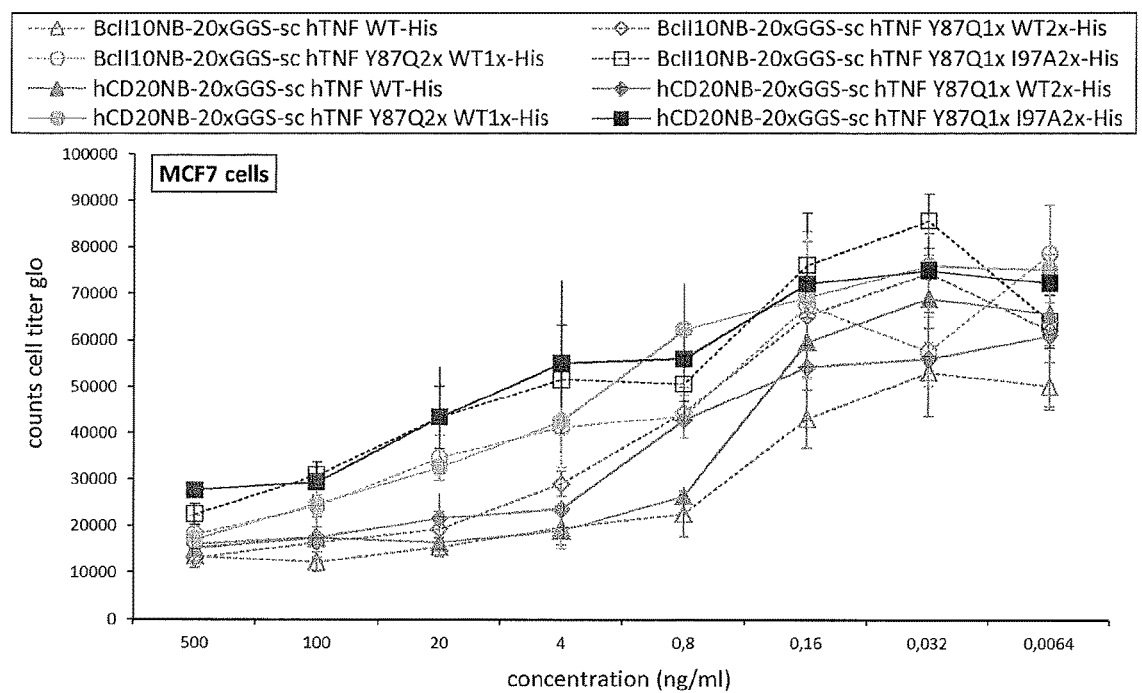
FIG. 11: Toxicity on MCF7 (panel A) or MCF7-hCD20 (panel B) cells of targeted modified TNFs containing sc hTNF with combined mutations (NB N-terminally of TNF).
Figure 11:
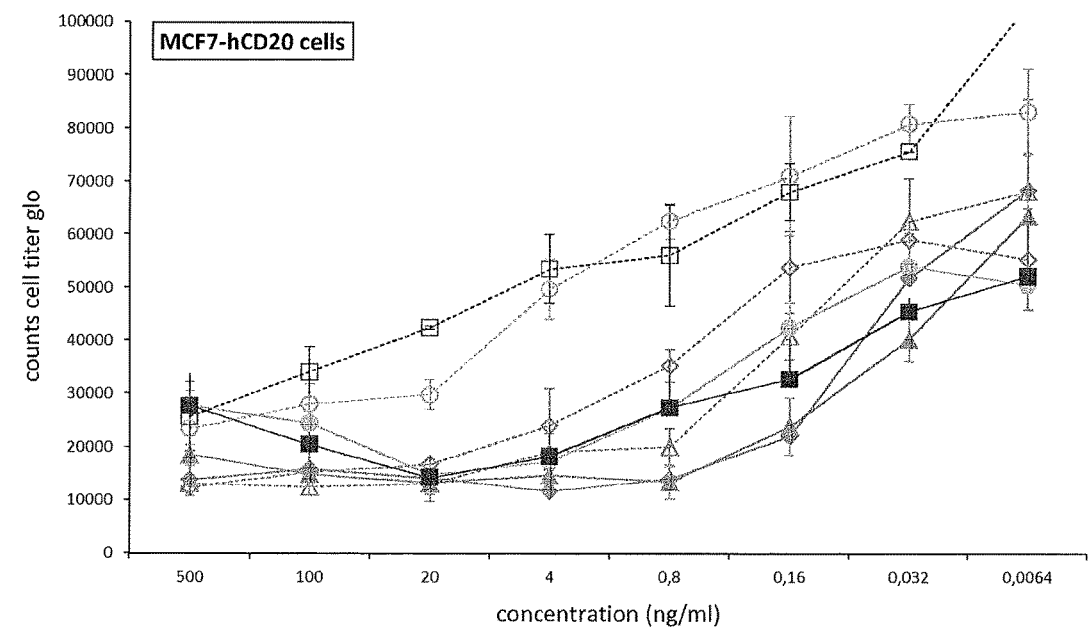

Despite the fact that the difference of targeted modified TNF versus non-targeted modified TNF is at least a 100-fold, some mutations show lower rescued activity than WT activity levels (Y87Q3x) which might affect its anti-tumor effects. Alternatively, some mutations still have some residual activity (I97S3x and Y115A3x) which might lead to some (systemic) toxicity when used in vivo. To overcome these potential drawbacks, we tested additional constructs by mutating different residues in the individual chains of sc hTNF in order to see whether the activity levels could thus be further modulated. As shown in FIG. 11, combining different mutations in the single chain can alter the residual activity on non-targeted cells and the level of reactivation upon targeting.

Example 10

Figure 12:
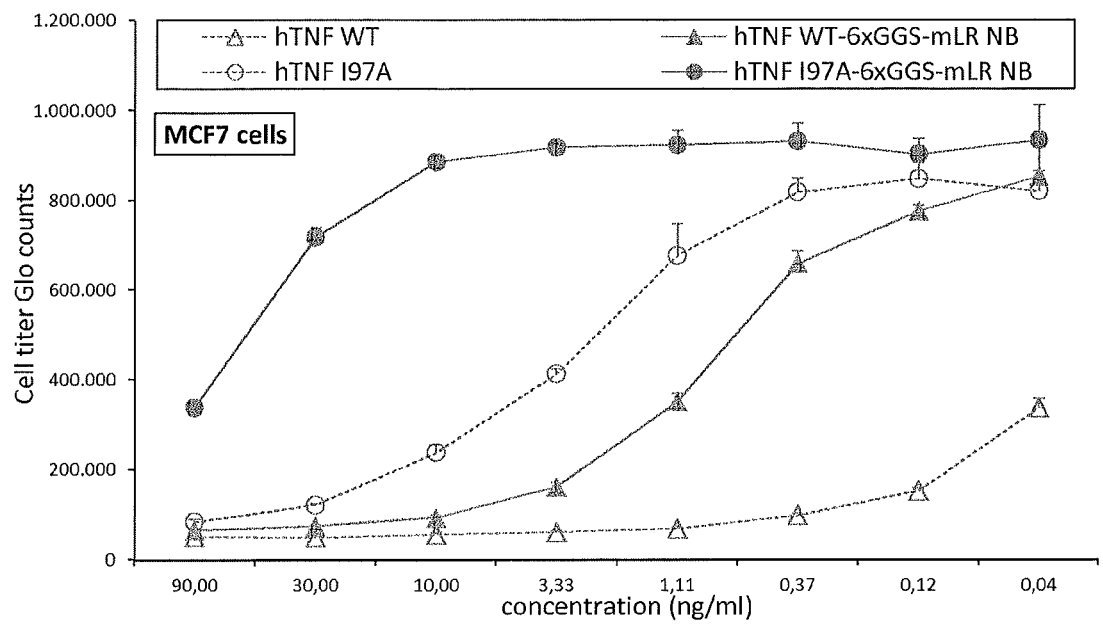
FIG. 12: Toxicity on MCF7 (panel A) or MCF7-mLR (panel B) cells of targeted modified TNF with individual trimerizing chains coupled to mLR NB (NB C-terminally of TNF).
Figure 12:
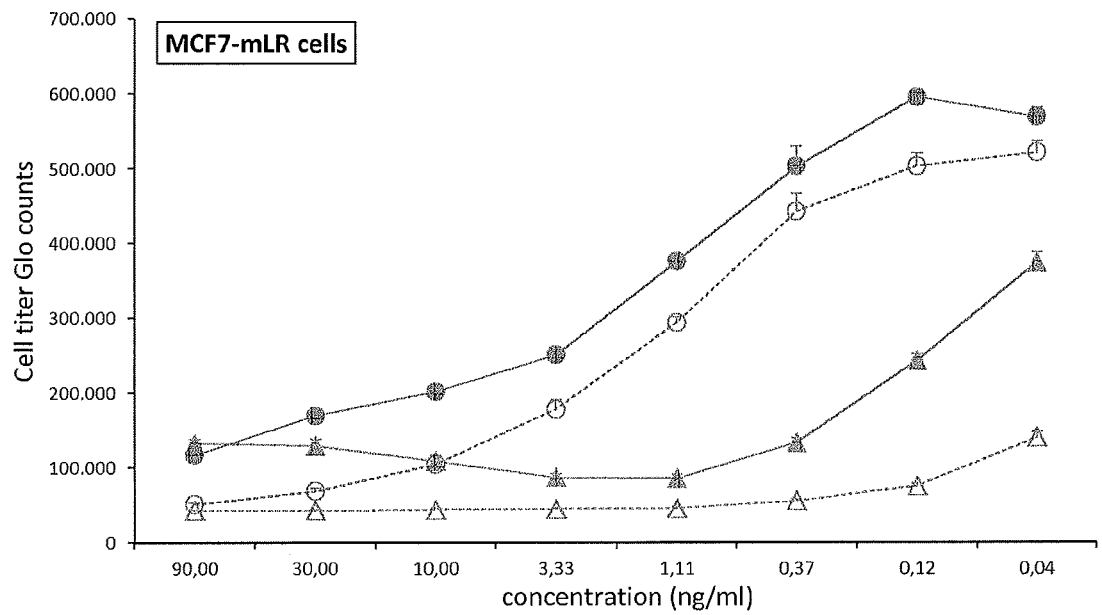

Comparison of Targeted Individual Trimerizing TNF Versus Single Chain Modified hTNF To compare the efficiency of targeted individual trimerizing versus single chain TNF, WT or I97A hTNF was coupled C-terminally to the mLR NB as a monomer. Their toxicity was tested on MCF7 cells and on MCF7 cells that express the mLR (MCF7-mLR), and is shown in FIG. 12. Also in the individual trimerizing form, the I97A mutation is toxic on MCF7 cells but to a lesser extent than WT hTNF (FIG. 8A & FIG. 12A). Moreover, when coupled C-terminally to the mLR nanobody, individual trimerizing—but not single chain—TNF becomes less toxic on MCF7 cells, and this is the case both for WT and I97A (FIG. 8A & FIG. 12A). Most probably, the 3 nanobodies present in the hTNF trimer formed with the individual trimerizing TNF-mLR NB constructs are sterically hindering the binding of hTNF to its receptor. This reduced activity can, however, be reverted by targeting to the mLR on MCF7-mLR cells (FIG. 12B). Interestingly, this offers a further level of modulation of activity: one can combine different mutations, as well as use the sterical hindrance to influence residual activity and level of reactivation upon targeting.

Figure 13:
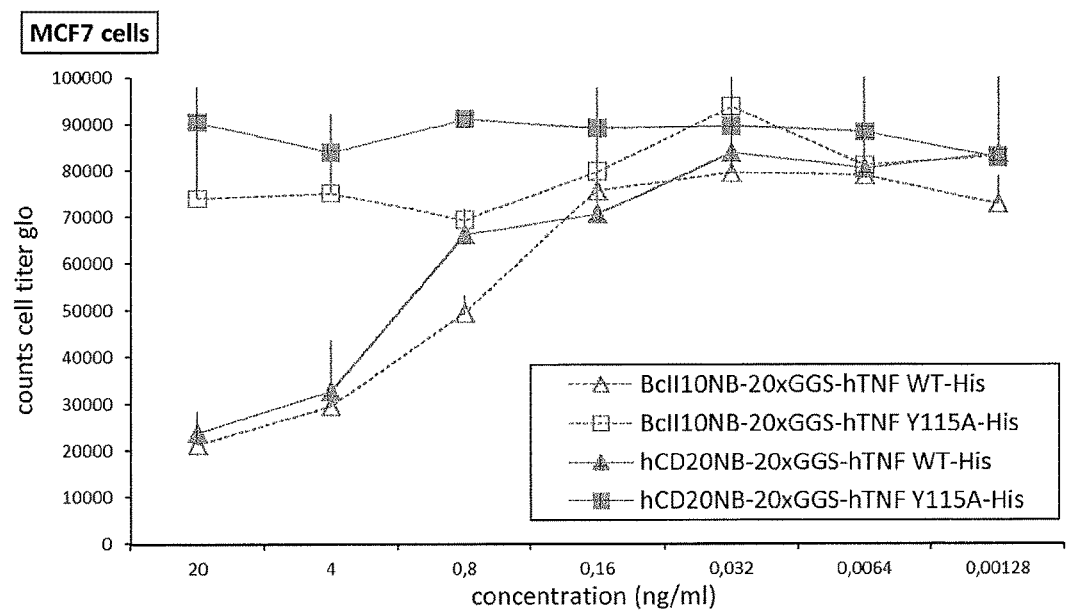
FIG. 13: Toxicity on MCF7 (panel A) or MCF7-hCD20 (panel B) cells of targeted modified TNF with individual trimerizing chains coupled to hCD20 NB (NB N-terminally of TNF).
Figure 13:
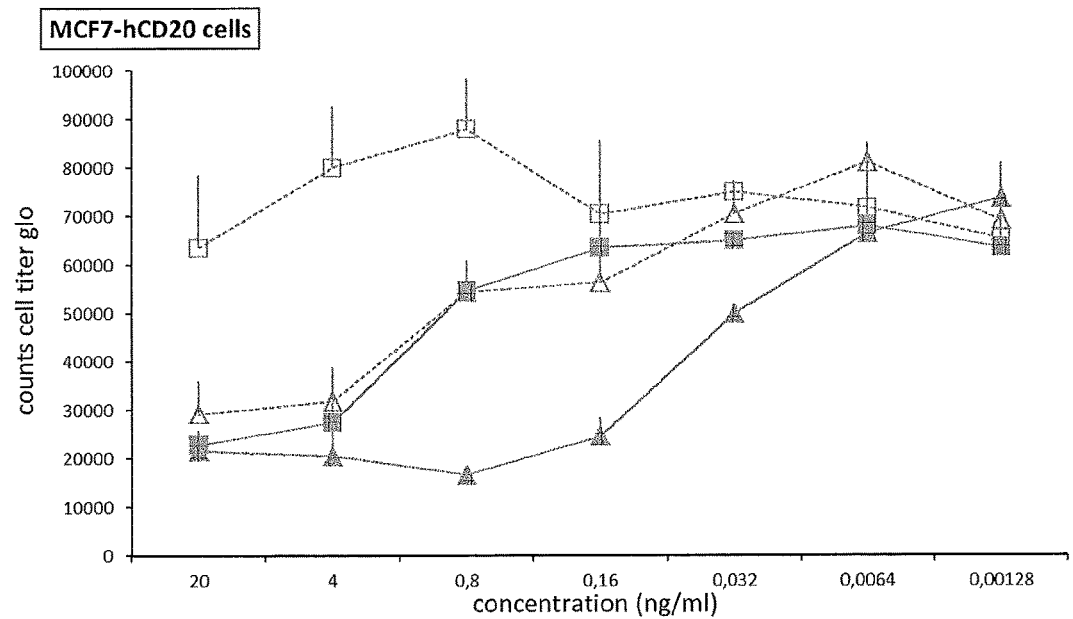

To address whether this is a general phenomenon, we coupled individual trimerizing WT and Y115A hTNF N-terminally to Bcl10 or hCD20 nanobody and tested their toxicity on MCF7 and MCF7-hCD20 cells. As shown in FIG. 13A, this coupling does not affect the toxicity of individual trimerizing WT or Y115A3x hTNF. Moreover, upon targeting, individual trimerizing Y115A3x hTNF becomes as active as non-targeted individual trimerizing WT hTNF (FIG. 13B).

Example 11

Assessment of in vivo Toxicity of Targeted Modified hTNF

To evaluate the toxicity of hTNF mutants preclinically is not evident, since TNF displays a remarkable species specificity in mice. In contrast to mTNF, hTNF only induces lethality at extremely high doses (Brouckaert et al. 1992). Although the reason for this species specificity was long thought to be caused by hTNF not interacting with the murine TNF-R2, pharmacokinetic studies have shown that hTNF is cleared much faster than mTNF in mice and that the consequential limited hTNF exposure is responsible for its lack of morbidity (Ameloot et al. 2002).

Figure 14:
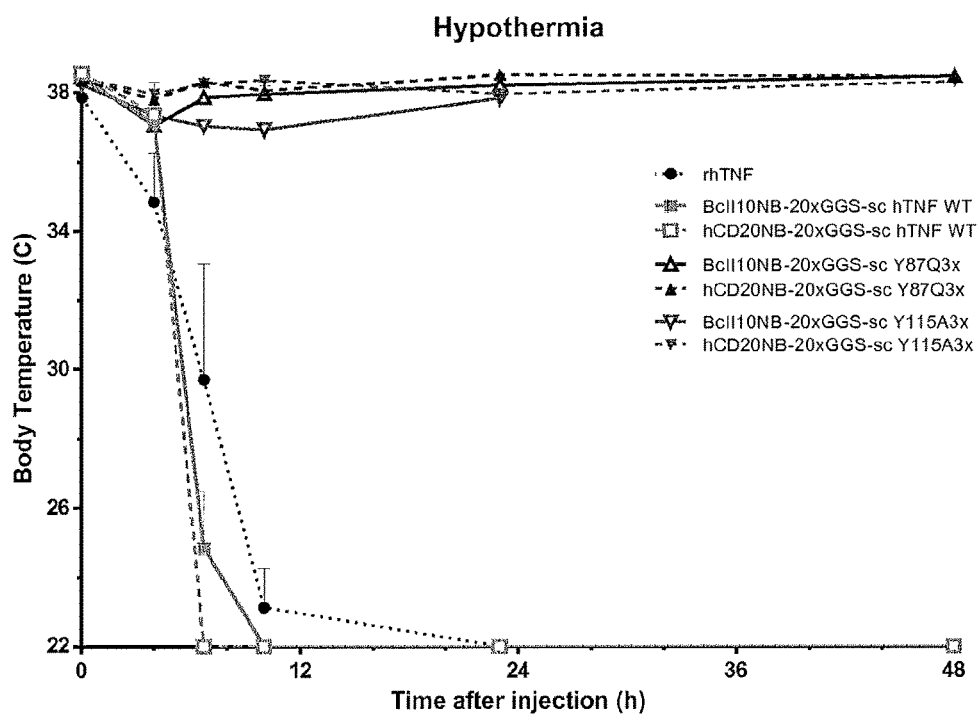
FIG. 14: Comparison of the in vivo toxicity of WT hTNF versus targeted WT and modified sc hTNFs coupled to hCD20 or control BclI10 NB (NB N-terminally of TNF). (A) Hypothermia (B) Mortality.
Figure 14:
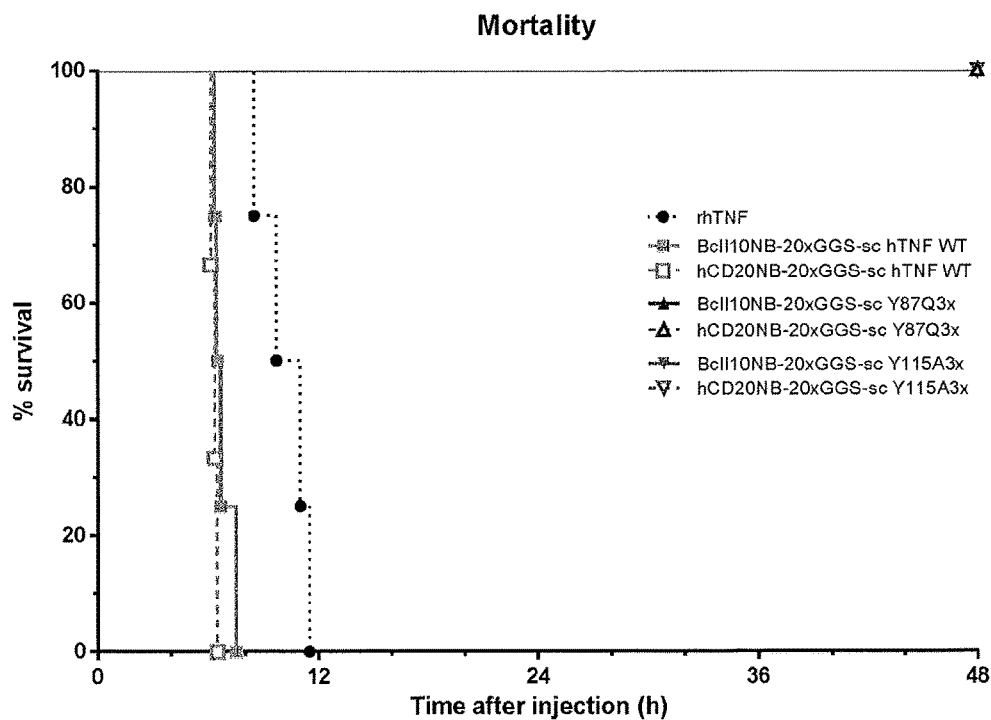

Nevertheless, when treated with a sensitizing agent such as D-galactosamine, species specificity is abolished and extremely low doses (≤500 ng) of hTNF are equally lethal as mTNF (Broeckaert et al., 1992). To assess the in vivo toxicity of the various targeted modified hTNFs, we therefore injected mice intraperitoneally with 500 ng of either recombinant (r) hTNF, sc hTNF WT or sc mutant hTNF (Y87Q3x or Y115A3x). The sc WT and modified hTNF were coupled N-terminally to either BclI10 or to hCD20 NB. As shown in FIG. 14, sc WT hTNF is at least as toxic as rhTNF, causing severe hypothermia and mortality within 10 h after injection. Targeted modified hTNF Y87Q3x and Y115A3x did not cause any signs of morbidity (pilo-erection, tremor, lethargy, loss of grooming or drop in body temperature; see FIG. 14A for the latter).

Example 12

Assessment of in vivo Toxicity and Anti-tumor Effect of Targeted Modified mTNF

Figure 15:
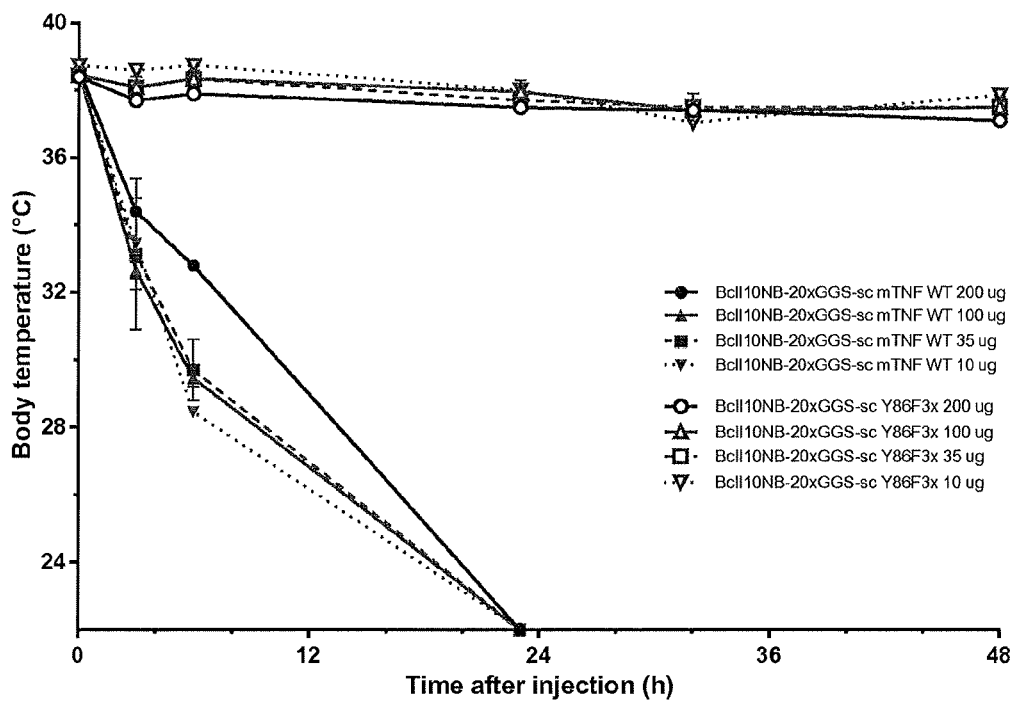
FIG. 15: In vivo toxicity of WT or modified (Y86F3x) sc mouse (m)TNF coupled to control BclI10 NB (NB N-terminally of TNF). (A) Hypothermia (B) Mortality.
Figure 15:
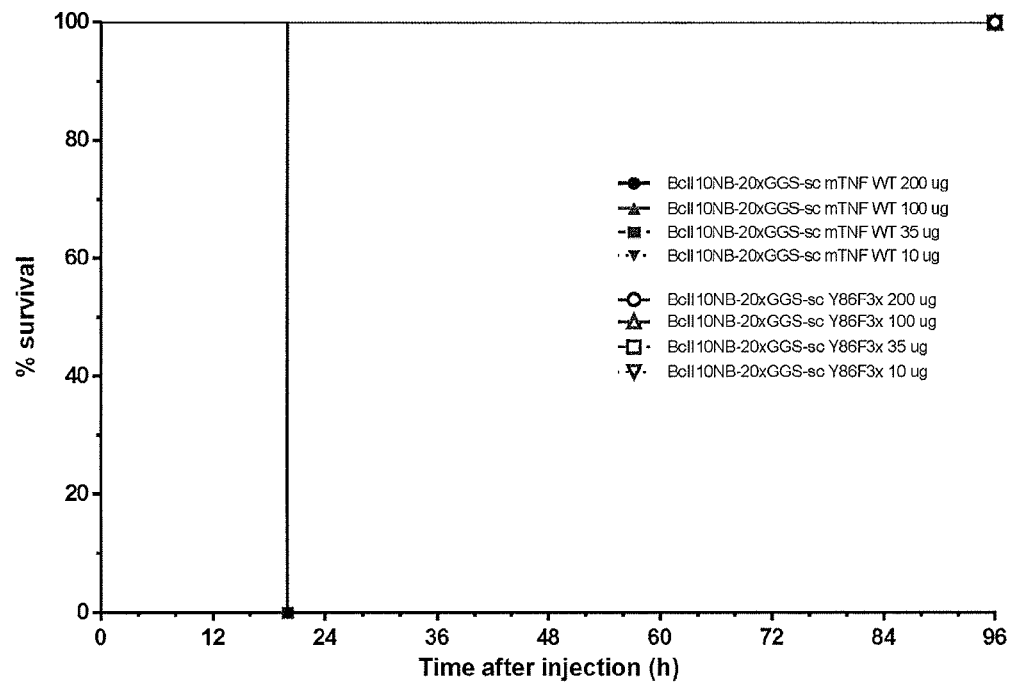

As already mentioned, in vivo toxicity of hTNF cannot be easily studied in mice. Therefore, as well as because of anticipated anti-tumor experiments in immunocompetent syngeneic mice, we decided to mutate residues of mTNF homologous to the ones we selected for hTNF (see example 5). As illustrated in FIG. 15, BclI10NB-sc mTNF WT caused severe morbidity (FIG. 15A) and 100% mortality (FIG. 15B) when injected intravenously in doses as low as 10 μg. In contrast, BclI10NB-sc mTNF Y86F3x did not induce mortality (FIG. 15B) nor cause any signs of toxicity (pilo-erection, tremor, lethargy, loss of grooming or drop in body temperature; see FIG. 15A for the latter), not even when injected as an intravenous bolus of 200 μg.

Figure 16:
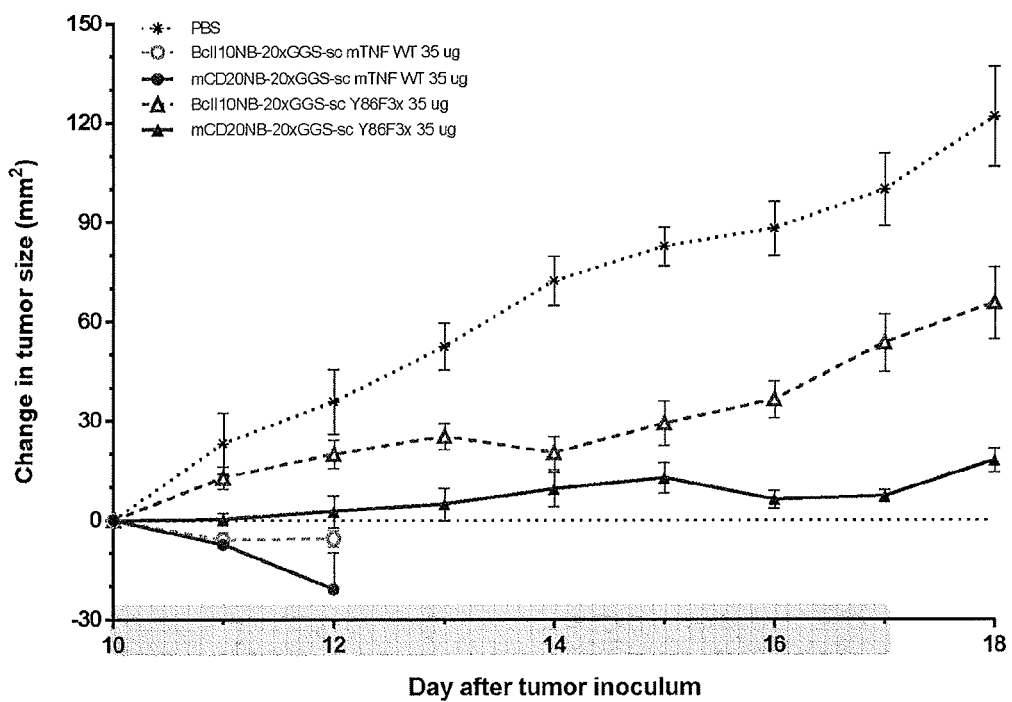
FIG. 16: In vivo anti-tumor effect of WT or modified (Y86F3x) sc mouse (m)TNF coupled to mCD20 or control BclI10 NB (NB N-terminally of TNF). (A) Tumor growth (B) Mortality.
Figure 16:
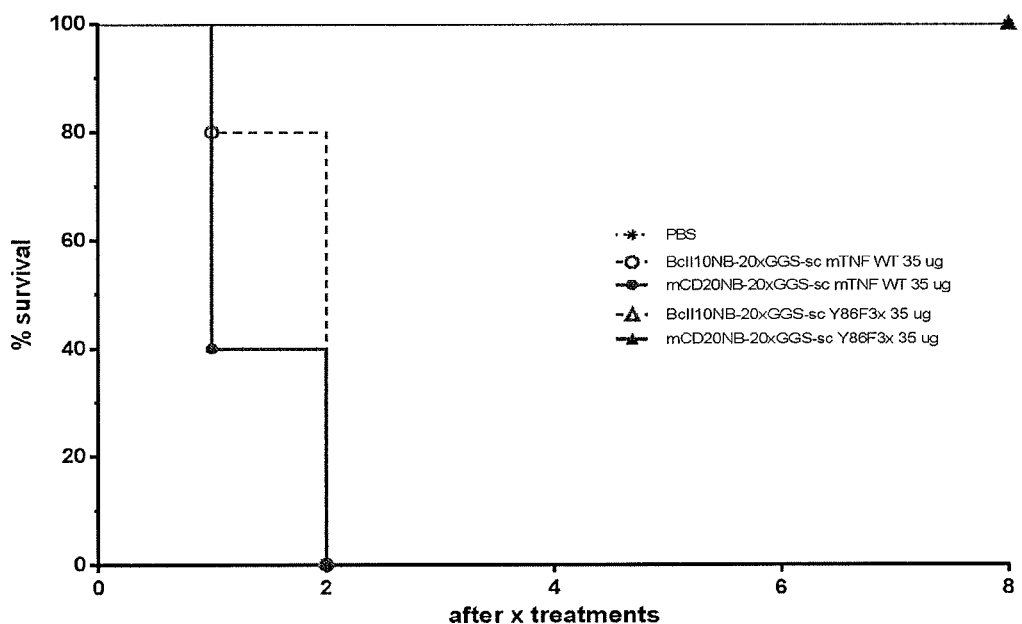

Nevertheless, when injected daily paralesionally in a dose of 35 μg in B16BI6-mCD20-tumor bearing mice, nanobody-coupled sc mTNF Y86F3x could still reduce/prevent tumor growth, especially when targeted to mCD20 (FIG. 16A). The effect of non-targeted mutant TNF on tumor growth (FIG. 16A) is due to the high dose (35 μg) used, as lower doses more closely mimic PBS-treated animals (data not shown). Daily treatment with the NB-sc mTNF Y86F3x did not cause any signs of morbidity or mortality, while tumor-bearing mice treated with NB-sc mTNF WT succumbed after 1 or 2 injections (FIG. 16B).

REFERENCES

Ameloot, P., Takahashi N., Everaerdt, B., Hostens, J., Eugster, H. P., Fiers, W., and Brouckaert, P. (2002). Bioavailability of recombinant tumor necrosis factor determines its lethality in mice. Eur J Immunol, 32, 2759-65.

Arap, W., Pasqualini, R. and Ruoslahti, E. 51998). Cancer treatment by targeted drug delivery to tumor vasculature in a mouse model. Science, 279, 377-380.

Ashkenazi, A. & Herbst, R. S. To kill a tumor cell: the potential of proapoptotic receptor agonists. J Clin Invest 118, 1979-1990 (2008).

Blake, A. W., McCartney, L., Flint, J., Bolam, D. N., Boraston, A. B., Gilbert, H. J. and Knox, J. P. (2006) Understanding the biological rationale for the diversity of cellulose-directed carbohydrate-binding molecules in prokaryotic enzymes. J. Biol. Chem. 281, 29321-29329. Boschert, V. et al. Single chain TNF derivatives with individually mutated receptor binding sites reveal differential stoichiometry of ligand receptor complex formation for TNFR1 and TNFR2. Cell Signal 22, 1088-1096 (2010).

Brecht et al., Peptide immobilization and characterization of binding specificity. J Biol Chem 268: 15425-15434

Brouckaert, P., Libert, C., Everaerdt, B. and Fiers W (1992). Selective species specificity of tumor necrosis factor for toxicity in the mouse. Lymphokine Cytokine Res, 11, 193-6.

Brown, K. C. (2010). Peptidic tumor targeting agents; the road from phagfe display selections to clinical applications. Curr. Pharm. Des. 16, 1040-1054.

Daburon, S. et al. Functional characterization of a chimeric soluble Fas ligand polymer with in vivo anti-tumor activity. PLoS One 8, e54000 (2013).

de Bruyn, M., Bremer, E. & Helfrich, W. Antibody-based fusion proteins to target death receptors in cancer. Cancer Lett 332, 175-183 (2013).

Dimitrov, D. S. (2009) Engineered CH2 domains (nanoantibodies). mAbs 1, 26-28.

Eyckerman, S., Waelput, W., Verhee, A., Broekaert, D., Vandekerckhove, J., and Tavernier, J. (1999). Eur. Cytok. Netw. 10, 549-559.

Falschlehner, C., Ganten, T. M., Koschny, R., Schaefer, U. & Walczak, H. TRAIL and other TRAIL receptor agonists as novel cancer therapeutics. Adv Exp Med Biol 647, 195-206 (2009).

Fox, N. L., Humphreys, R., Luster, T. A., Klein, J. & Gallant, G. Tumor Necrosis Factor-related apoptosis-inducing ligand (TRAIL) Receptor-1 and Receptor-2 agonists for cancer therapy. Expert Opin Biol Ther 10, 1-18 (2010).

Galle, P. R. et al. Involvement of the CD95 (APO-1/Fas) receptor and ligand in liver damage. J Exp Med 182, 1223-1230 (1995).

Gaur, U. & Aggarwal, B. B. Regulation of proliferation, survival and apoptosis by members of the TNF superfamily. Biochem Pharmacol 66, 1403-1408 (2003).

Ghahroudi A. M., Desmyter, A., Wyns, L., Hamers, R., Muyldermans, S. (1997). Selection and identification of single domain antibody fragments from camel heavy-chain antibodies. FEBS Lett. 414, 521-6

Gregorc, V. et al. Phase 1b study of NGR-hTNF, a selective vascular targeting agent, administered at low doses in combination with doxorubicin to patients with advanced solid tumours. Br J Cancer 101, 219-224 (2009).

Hehlgans, T. & Pfeffer, K. The intriguing biology of the tumour necrosis factor/tumour necrosis factor receptor superfamily: players, rules and the games. Immunology 115, 1-20 (2005).

Huang, Y. & Sheikh, M. S. TRAIL death receptors and cancer therapeutics. Toxicol Appl Pharmacol 224, 284-289 (2007).

Johnstone, R. W., Frew, A. J. & Smyth, M. J. The TRAIL apoptotic pathway in cancer onset, progression and therapy. Nat Rev Cancer 8, 782-798 (2008).

Koivunen, E., Wang, B. and Ruoslahti, E. (1994). Isolation of a highly specific ligand for the α5β1 integrin from a phage library. J. Cell. Biol. 124, 373-380.

Kolmar, H. (2008) Alternative binding proteins: biological activity and therapeutic potential of cysteine-knot miniproteins. FEBS J. 275, 2684-2690.

Lejeune, F. J., Lienard, D., Matter, M. & Ruegg, C. Efficiency of recombinant human TNF in human cancer therapy. Cancer Immun 6, 6 (2006).

Li, M. et al. Phase II multicenter, randomized, double-blind study of recombinant mutated human tumor necrosis factor-alpha in combination with chemotherapies in cancer patients. Cancer Sci 103, 288-295 (2012).

Liu, Y. et al. The antimelanoma immunocytokine scFvMEL/TNF shows reduced toxicity and potent antitumor activity against human tumor xenografts. Neoplasia 8, 384-393 (2006).

Loetscher, H., Stueber, D., Banner, D., Mackay, F. & Lesslauer, W. Human tumor necrosis factor alpha (TNF alpha) mutants with exclusive specificity for the 55-kDa or 75-kDa TNF receptors. J Biol Chem 268, 26350-26357 (1993).

Nygren, P-A. (2008) Alternative binding proteins: affibody binding proteins developed from a small three-helix bundle scaffold. FEBS J. 275, 2668-2676.

Ogasawara, J. et al. Lethal effect of the anti-Fas antibody in mice. Nature 364, 806-809 (1993).

Pardon, E., Laeremans, T., Triest, S., Rasmussen, S. G. F., Wohlkonig, A., Ruf, A., Muyldermans, S., Hol, W. G. J, Kobilka, B. K. and Steyaert, J. (2014). A general protocol for the generation of Nanobodies for structural biology. Nature Protocols 9, 674-693

Roberts, N. J., Zhou, S., Diaz, L. A., Jr. & Holdhoff, M. Systemic use of tumor necrosis factor alpha as an anticancer agent. Oncotarget 2, 739-751 (2011).

Roccaro A M, Hideshima T, Raje N, Kumar S, Ishitsuka K, Yasui H, Shiraishi N, Ribatti D, Nico B, Vacca A, Dammacco F, Richardson P G, Anderson K C. Bortezomib mediates antiangiogenesis in multiple myeloma via direct and indirect effects on endothelial cells. Cancer Res. 2006; 66(1):184-91.

Scatchard G. Ann New York Acad Sci 1949; 51, 660-72.

Schmidt T, Carmeliet P. Angiogenesis: a target in solid tumors, also in leukemia? Hematology Am Soc Hematol Educ Program. 2011; 2011:1-8.

Siegemund, M. et al. Superior antitumoral activity of dimerized targeted single-chain TRAIL fusion proteins under retention of tumor selectivity. Cell Death Dis 3, e295 (2012).

Skerra, A. (2008) Alternative binding proteins: anticalins—harnessing the structural plasticity of the lipocalin ligand pocket to engineer novel binding activities. FEBS J. 275, 2677-2683.

Stump, M. T., Binz, H. K., Amstutz, P. (2008) DARPins: a new generation of protein therapeutics. Drug iscov. Today 13, 695-701.

Tramontano, A., Bianchi, E., Venturini, S., Martin, F., Pessi, A and Sollazzo, M. (1994) The making of the minibody: an engineered beta-protein for the display of confromationally constrained peptides. J. Mol. Recognition 7, 9-24.

Vanden Berghe, W. et al. p38 and extracellular signal-regulated kinase mitogen-activated protein kinase pathways are required for nuclear factor-kappaB p65 transactivation mediated by tumor necrosis factor. J Biol Chem 273, 3285-3290 (1998).

Vaneycken, I. et al. Preclinical screening of anti-HER2 nanobodies for molecular imaging of breast cancer. FASEB J 25, 2433-2446 (2011).

van Horssen, R., Ten Hagen, T. L. & Eggermont, A. M. TNF-alpha in cancer treatment: molecular insights, antitumor effects, and clinical utility. Oncologist 11, 397-408 (2006).

Wang, H., Yan, Z., Shi, J., Han, W. & Zhang, Y. Expression, purification, and characterization of a neovasculature targeted rmhTNF-alpha in *Escherichia coli*. Protein Expr Purif 45, 60-65 (2006).

Welti J, Loges S, Dimmeler S, Carmeliet P. Recent molecular discoveries in angiogenesis and antiangiogenic therapies in cancer. J Clin Invest. 2013; 123(8):3190-200.

Yang, Y. H., Rajaiah, R., Ruoslahti, E. and Moudgil, K. D. (2011). Peptides targeting inflamed synovial vasculature attenuate autoimmune arthritis. PBNAS 108, 12857-12862.

Zabeau, L. et al. Selection of non-competitive leptin antagonists using a random nanobody-based approach. Biochem J 441, 425-434 (2012).

The invention claimed is:

1. A composition comprising a proteinaceous construct, comprising
   (i) a single chain polypeptide comprising three modified human TNFs, wherein:
      each modified human TNF comprises a modified amino acid residue by substitution at the Y87 position relative to wild type human TNF (SEQ ID NO: 14), the substitution being selected from Q, L, A, and F and
      the modified human TNFs have reduced affinity towards their receptor as compared to wild type human TNF; and
   (ii) a targeting moiety that is an antibody or a variable domain of a camelid heavy chain antibody (VHH) directed to a neo-vasculature tissue or cancer tissue specific marker,
   wherein the composition has significant biological activity towards cells that are targeted by the targeting moiety.

2. The composition of claim 1, wherein the targeting moiety is a VHH.

3. The composition of claim 1, wherein the targeting moiety is directed towards CD20.

4. The composition of claim 1, wherein the targeting moiety is directed towards Her2.

5. The composition of claim 3, wherein the targeting moiety is a VHH.

6. The composition of claim 4, wherein the targeting moiety is a VHH.

* * * * *